(12) United States Patent
Konno

(10) Patent No.: US 10,751,020 B2
(45) Date of Patent: Aug. 25, 2020

(54) X-RAY DETECTOR, X-RAY CT DEVICE, X-RAY DETECTION METHOD, AND X-RAY DETECTION PROGRAM

(71) Applicant: Hitachi, Ltd., Tokyo (JP)

(72) Inventor: Yasutaka Konno, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 212 days.

(21) Appl. No.: 16/077,552

(22) PCT Filed: Feb. 3, 2017

(86) PCT No.: PCT/JP2017/003908
§ 371 (c)(1),
(2) Date: Aug. 13, 2018

(87) PCT Pub. No.: WO2017/150068
PCT Pub. Date: Sep. 8, 2017

(65) Prior Publication Data
US 2019/0029628 A1    Jan. 31, 2019

(30) Foreign Application Priority Data

Feb. 29, 2016  (JP) .................................. 2016-037237

(51) Int. Cl.
*A61B 6/00*         (2006.01)
*H04N 5/347*        (2011.01)
(Continued)

(52) U.S. Cl.
CPC ............ *A61B 6/5258* (2013.01); *A61B 6/032* (2013.01); *A61B 6/4233* (2013.01);
(Continued)

(58) Field of Classification Search
CPC ....... A61B 6/542; A61B 6/4241; A61B 6/032; A61B 6/5258; A61B 6/4233
See application file for complete search history.

(56) References Cited

U.S. PATENT DOCUMENTS 9,354,184 B2 * 5/2016 Dowaki .................. H04N 5/32
9,578,262 B2 * 2/2017 Dowaki .................. H04N 5/32
(Continued)

FOREIGN PATENT DOCUMENTS

JP    2012231210 A    11/2012
JP    2014050716 A     3/2014

OTHER PUBLICATIONS

International Search Report for PCT Application No. PCT/JP2017/003908, dated Apr. 18, 2017, 1 page.

*Primary Examiner* — David P Porta
*Assistant Examiner* — Djura Malevic
(74) *Attorney, Agent, or Firm* — Baker Botts L.L.P.

(57) ABSTRACT

There is disclosed an X-ray detector that includes a detection section, an addition rate determination section, an addition section, and a position information storage section in order to enhance the accuracy of interpolation of an output signal from a defective element and suppress artifacts with ease without increasing, for example, the length of processing time, the number of processing circuits, and the amount of interpolation data. The detection section includes a plurality of arrays of detection element groups that are each formed of a plurality of detection elements in correspondence with one pixel. The addition rate determination section determines addition rates for output signals of the detection elements. The addition section calculates the signal value of each pixel of a projection image by adding the output signals of the detection elements belonging to the detection element groups in accordance with the addition rates. The position information storage section stores pixel position information and defective element position information. The pixel position information indicates the positional relationship between the pixel and the detection elements. The defective element position information indicates the position of a defective element. Based on the pixel position information and the defective element position information, the addition rate determination section determines the addition rate for the output signal of the defective element and the addition (Continued)

rate for the output signal of a diagonal detection element positioned symmetrically with respect to the defective element in such a manner that the addition rates are equal and lower than the addition rates for the other detection elements and that the addition rates for the other detection elements are substantially equal.

14 Claims, 24 Drawing Sheets

(51) Int. Cl.
    *H04N 5/367*     (2011.01)
    *A61B 6/03*     (2006.01)
    *H04N 5/32*     (2006.01)

(52) U.S. Cl.
    CPC ............ *A61B 6/4241* (2013.01); *A61B 6/542* (2013.01); *A61B 6/586* (2013.01); *H04N 5/32* (2013.01); *H04N 5/347* (2013.01); *H04N 5/367* (2013.01)

(56) References Cited

U.S. PATENT DOCUMENTS

| | | | | |
|---|---|---|---|---|
| 10,448,914 | B2* | 10/2019 | Spahn | H04N 5/32 |
| 2002/0190215 | A1* | 12/2002 | Tashiro | H01L 27/14658 250/370.11 |
| 2008/0117318 | A1* | 5/2008 | Aoki | H04N 5/367 348/246 |
| 2008/0273101 | A1* | 11/2008 | Takenaka | H04N 5/361 348/243 |
| 2009/0021607 | A1* | 1/2009 | Takenaka | A61B 6/00 348/231.99 |
| 2011/0235775 | A1 | 9/2011 | Tada | |
| 2012/0006993 | A1* | 1/2012 | Arishima | H04N 5/32 250/369 |
| 2013/0193334 | A1* | 8/2013 | Dowaki | H04N 5/361 250/370.09 |
| 2017/0020475 | A1 | 1/2017 | Spahn | |

\* cited by examiner

| 0 | 1 | 1 |
|---|---|---|
| 1 | 1 | 1 |
| 1 | 1 | 1 |

(b)

| 0 | 1 | 1 |
|---|---|---|
| 1 | 1 | 1 |
| 1 | 1 | 0 |

(c)

| 0 | 1 | 1 |
|---|---|---|
| 1 | 3 | 1 |
| 1 | 1 | 0 |

(d)

| 0 | 3 | 0 |
|---|---|---|
| 1 | 1 | 1 |
| 1 | 1 | 1 |

(e)

| 0 | 1 | 1 |
|---|---|---|
| 3 | 1 | 1 |
| 0 | 1 | 1 |

(f)

| 0 | 5/3 | 2/3 |
|---|---|---|
| 5/3 | 5/3 | 1 |
| 2/3 | 1 | 2/3 |

| 0 | 1 | 1 |
|---|---|---|
| 1 | 1 | 1 |
| 1.5 | 0 | 0.5 |

(b)

| 0 | 0 | 1 |
|---|---|---|
| 1 | 1 | 1 |
| 1 | 0 | 0 |

X-RAY DETECTOR, X-RAY CT DEVICE, X-RAY DETECTION METHOD, AND X-RAY DETECTION PROGRAM

CROSS-REFERENCE TO RELATED APPLICATIONS

This application is a national phase claiming the benefit of and priority to International Patent Application No. PCT/JP2017/003908, entitled "X-RAY DETECTOR, X-RAY CT DEVICE, X-RAY DETECTION METHOD, AND X-RAY DETECTION PROGRAM", filed Feb. 3, 2017, which claims priority to Japanese Patent Application No. 2016-037237, filed Feb. 29, 2016, which are hereby incorporated by reference in their entireties.

TECHNICAL FIELD

The present invention relates to an X-ray detector, and more particularly to an X-ray detector for interpolating a defect in an output signal that is caused by a defective element.

BACKGROUND ART

A certain known X-ray CT device calculates an X-ray absorption coefficient (linear attenuation coefficient) from a projection image that is an X-ray transmission image of a test subject and captured from a plurality of directions, and acquires a reconstructed image that is a tomographic image of the test subject.

An integrated X-ray detector applied to such an X-ray CT device includes a plurality of detection elements, converts X-ray energy transmitted through the test subject to an electrical signal on an individual detection element basis, and acquires a projection image by outputting an integrated signal that has been integrated for a predetermined period of time. In this instance, the detection elements may include defective detection elements (hereinafter referred to as "defective elements"). The defective elements may shift a pixel sampling position, and thus alter an output value. As a result, artifacts may occur in the projection image.

Under the above circumstances, if a pixel defect occurs in a projection image due to a defective element, an imaging device described, for example, in Patent Literature 1 (PTL 1) estimates an output signal of the defective element from an output signal of a normal detection element, and corrects the influence exerted on elements surrounding the defective element by the defective element by using an influence quantity parameter that is predefined for the estimated value.

Meanwhile, an X-ray CT device having a photon-counting X-ray detector for measuring the number of X-ray photons has been developed in recent years. An X-ray CT device with a photon-counting X-ray detector is advantageous in being able to create an energy-specific pseudo-monochromatic reconstructed image, which cannot be acquired by an X-ray CT device having an integrated X-ray detector, and a reconstructed image of an absorption coefficient other than those indicating the distribution, for example, of atomic numbers (these images are hereinafter referred to as "multi-energy images").

An embodiment of an X-ray CT device to which a photon-counting detector is applied allocates a plurality of minute detection elements to each pixel, measures the number of X-ray photons on an individual detection element basis, and adds up the resulting output values to determine the output of each pixel for a projection image. When the photon-counting detector is applied, a pile-up can be reduced in an X-ray CT device or other device using a very high X-ray dose rate. Further, reducing the size of the detection elements increases the number of detection elements used to capture an image of a particular area range. However, when the size is increased as needed at the photon-counting detector, that is, at the X-ray CT device in terms of the projection image, it is possible to suppress an increase, for example, in the amount of data to be processed by the X-ray CT device, the number of processing circuits, the number of processing steps, and the length of processing time.

CITATION LIST

Patent Literature

PTL 1: Japanese Patent Application Laid-Open No. 2012-231210

SUMMARY OF INVENTION

Technical Problem

However, the photon-counting detector allocates a plurality of minute detection elements to each pixel as described above. Therefore, the photon-counting detector has more detection elements than an integrated detector, and has a relatively high percentage of defective elements due to an abnormality, for example, in a readout circuit or in a detection section. Consequently, if a technology for interpolating a pixel defect, which is incorporated, for instance, in the imaging device described in Patent Literature 1 (PTL 1), is applied as is, for example, an increased amount of processing time, an increased number of processing circuits, and an increased volume of interpolation data are required. This results, for example, in a decrease in processing speed, an increase in device cost, and an increase in the number of man-hours.

The present invention has been made in view of the above circumstances. An object of the present invention is to avoid an increase, for example, in the length of processing time, the number of processing circuits, and the amount of interpolation data, enhance the accuracy of interpolation of defective elements, and suppress artifacts with ease.

Solution to Problem

In order to solve the above problem, the present invention provides the following means.

According to an aspect of the present invention, there is provided an X-ray detector including a detection section, an addition rate determination section, an addition section, and a position information storage section. The detection section includes a plurality of detection element groups obtained by forming a two-dimensional array of detection elements for detecting X-rays, and forms a plurality of arrays of the detection element groups corresponding to one pixel. The addition rate determination section determines addition rates for output signals of the detection elements. The addition section calculates the signal value of each pixel of a projection image by adding the output signals of the detection elements belonging to the detection element groups in accordance with the addition rates. The position information storage section stores pixel position information and defective element position information. The pixel position information indicates the positional relationship between the pixel and the detection elements belonging to a detection element group corresponding to the pixel. The defective element position information indicates the position of a defective element included in the detection element group. Based on the pixel position information and the defective element position information, the addition rate determination section determines the addition rate for the output signal of the defective element included in a pixel targeted for signal value calculation and the addition rate for the output signal of a diagonal detection element positioned symmetrically with respect to the defective element about the center of the pixel targeted for signal value calculation in such a manner that the addition rates are equal and lower than the addition rates for the other detection elements and that the addition rates for the other detection elements are substantially equal.

Advantageous Effects of Invention

The present invention makes it possible to avoid an increase, for example, in the length of processing time, the number of processing circuits, and the amount of interpolation data, enhance the accuracy of interpolation of defective elements, and suppress artifacts with ease.

BRIEF DESCRIPTION OF DRAWINGS

FIG. 11 illustrates an exemplary addition rate for the detection elements in the detection section of the X-ray detector according to the first embodiment of the present invention, (a) illustrates the addition rate in a pixel when (−1, 1) in FIG. 9 is a defective element and the addition rate is 0, (b) illustrates the addition rate when the addition rate for the defective element (−1, 1) and its diagonal detection element (1, −1) is 0, and (c) to (f) illustrate an example in which the addition rate is calculated by extrapolation.

FIG. 15 is a diagram illustrating an exemplary array of the detection elements in the detection section of the X-ray detector according to the first embodiment of the present invention and, in particular, the addition rate for the detection elements.

FIG. 17 illustrates an example of the addition rate in a case where the detection elements are arrayed as illustrated in FIG. 16, (a) illustrates an example in which the addition rate for the detection elements around defective elements is increased, and (b) illustrates an example in which the addition rate for a diagonal detection element, which is positioned diagonally relative to a defective element, is 0.

DESCRIPTION OF EMBODIMENTS

An embodiment of the present invention will now be described with reference to the accompanying drawings.

An X-ray detector according to the present invention includes a detection section, an addition rate determination section, an addition section, and a position information storage section. The detection section includes a plurality of detection element groups obtained by forming a two-dimensional array of detection elements for detecting X-rays, and forms a plurality of arrays of the detection element groups corresponding to one pixel. The addition rate determination section determines addition rates for output signals of the detection elements. The addition section calculates the signal value of each pixel of a projection image by adding the output signals of the detection elements belonging to the detection element groups in accordance with the addition rates. The position information storage section stores pixel position information and defective element position information. The pixel position information indicates the positional relationship between a pixel and the detection elements belonging to a detection element group corresponding to the pixel. The defective element position information indicates the position of a defective element included in the detection element group. Based on the pixel position information and the defective element position information, the addition rate determination section determines the addition rate for the output signal of the defective element included in a pixel targeted for signal value calculation and the addition rate for the output signal of a diagonal detection element symmetrical with respect to the defective element about the center of the pixel targeted for signal value calculation in such a manner that the addition rates are equal and lower than the addition rates for the other detection elements, and determines the addition rates for the other detection elements in such a manner that they are substantially equal.

Embodiments of the present invention will now be described in more detail.

First Embodiment

The X-ray detector according to an embodiment of the present invention will now be described with reference to the accompanying drawings. The present embodiment will be described with reference to an example in which the X-ray detector is applied to an X-ray CT device.

Figure 1:
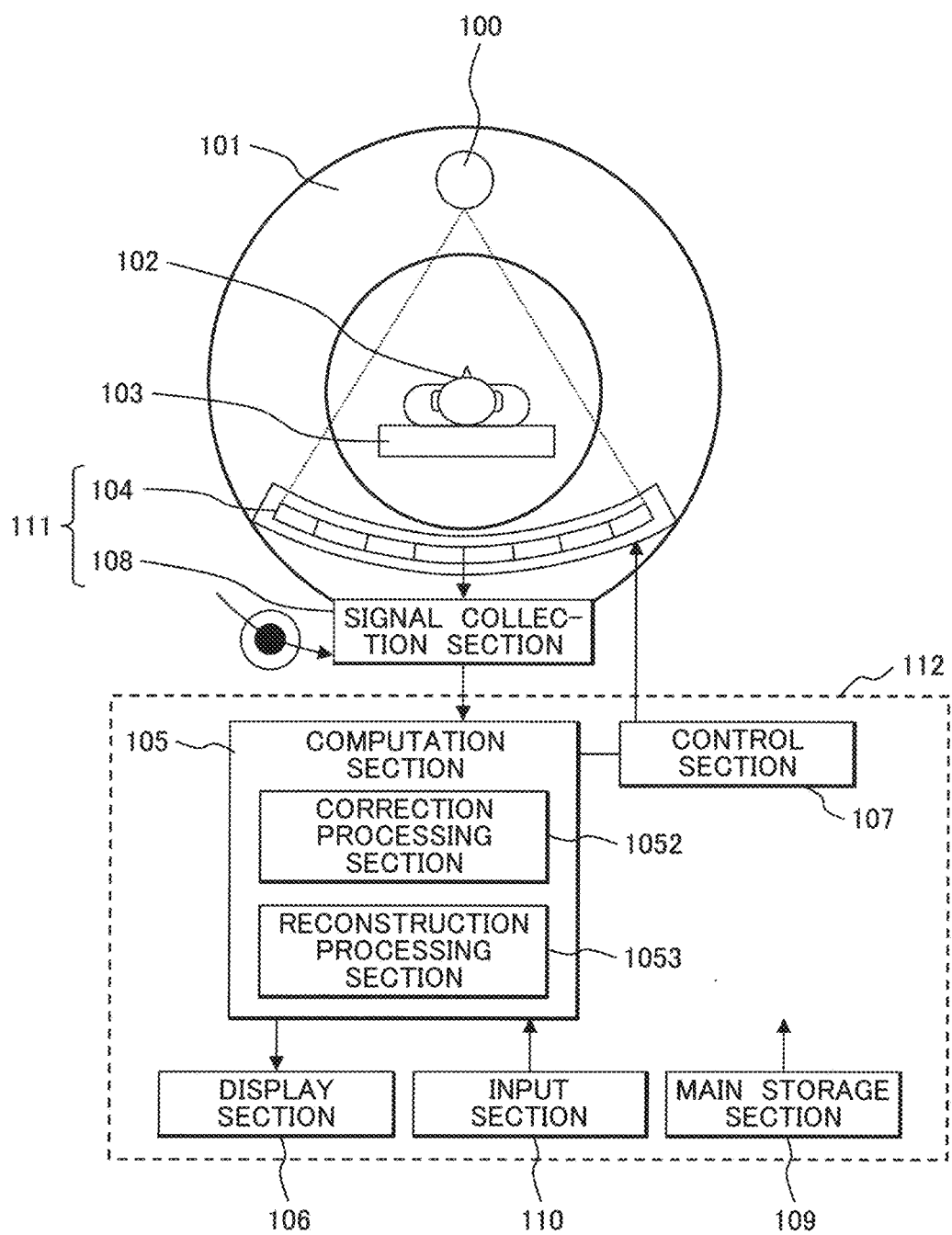
FIG. 1 is a block diagram illustrating an overview of an X-ray CT device to which an X-ray detector according to a first embodiment of the present invention is applied.

As illustrated in FIG. 1, the X-ray CT device includes an imaging system and a signal processing section 112. The imaging system includes an X-ray source 100, an X-ray detector 111, a gantry rotation section 101, and a bed top plate 103. The gantry rotation section 101 rotates around a predetermined rotation axis with the X-ray source 100 and a later-described detection section 104 of the X-ray detector 111 disposed to oppose each other. The bed top plate 103 is disposed within an opening in the gantry rotation section 101. The signal processing section 112 processes signals that are acquired by the X-ray detector 111 as the imaging system operates.

The X-ray source 100 allows an electron beam accelerated, for example, by a tube voltage to collide with a target metal, such as tungsten or molybdenum, and generates X-rays from a collision position (focal point).

The gantry rotation section 101 rotates around the predetermined rotation axis rotation axis with the X-ray source 100 and the detection section 104 disposed to oppose each other. The center of the gantry rotation section 101 is provided with an opening into which a test subject 102 is inserted. The bed top plate 103 on which the test subject 102 is laid is disposed in this opening. The bed top plate 103 and the gantry rotation section 101 are relatively movable in predetermined directions.

The X-ray detector 111 includes the detection section 104 and a signal collection section 108. A plurality of detection elements 400 are disposed in the detection section 104. The detection elements 400 are of the photon-counting type that detects incident X-ray photons, separates the X-ray photons into two energy ranges, and counts the number of X-ray photons. The signal collection section 108 collects projection images outputted from the detection elements 400. The X-ray detector 111 will be described in detail later.

The signal processing section 112 includes a computation section 105, a display section 106, a control section 107, a main storage section 109, and an input section 110.

In order to perform a predetermined computation process on collected signals, the computation section 105 includes a correction processing section 1052 and a reconstruction processing section 1053. The correction processing section 1052 performs a correction process on the signals collected by the signal collection section 108. The reconstruction processing section 1053 prepares a reconstructed image such as a multi-energy image.

The display section 106 displays, for example, a reconstructed image generated by the computation section 105. The control section 107 includes an X-ray control section, a readout control section, an imaging control section, and an overall control section. The X-ray control section controls the operation of a generation driving source for the X-ray source 100. The readout control section controls a signal readout operation of the X-ray detector 111. The imaging control section controls the rotation of the gantry rotation section 101 and the movement of the bed top plate 103. The overall control section provides overall control of the above sections. The main storage section 109 stores, for example, parameters and data used for the computation process in the computation section 105. The input section 110 inputs, for example, imaging conditions for the X-ray CT device.

The computation section 105 and the control section 107 can be partly or wholly configured as a system that includes a CPU (central processing unit), a memory, and the main storage section 109. Functions of individual sections included in the computation section 105 and the control section 107 can be implemented by allowing the CPU to load programs stored in the storage section in advance into the memory and execute the programs. Some of the functions may alternatively be implemented by hardware such as an ASIC (application-specific integrated circuit) or an FPGA (field-programmable gate array).

Unless otherwise stated, the following description assumes that elements included in the above-described imaging system, control section 107, and signal processing section 112 have the same configurations and functions as the elements included in a well-known X-ray CT device.

The X-ray detector 111 will now be described.

The X-ray detector 111 includes the detection section 104 and the signal collection section 108. The signal collection section 108 collects output signals from the detection elements 400 in the detection section 104 as projection images.

The detection section 104 includes a plurality of detection element groups obtained by forming a two-dimensional array of detection elements 400 for detecting X-rays, and forms a plurality of arrays of the detection element groups corresponding to one pixel of a projection image. Each of the detection elements 400 included in the detection section 104 is a so-called photon-counting detection element that detects incident X-ray photons, separates the incident X-ray photons into, for example, two energy ranges, and counts the number of incident X-ray photons.

Figure 2:
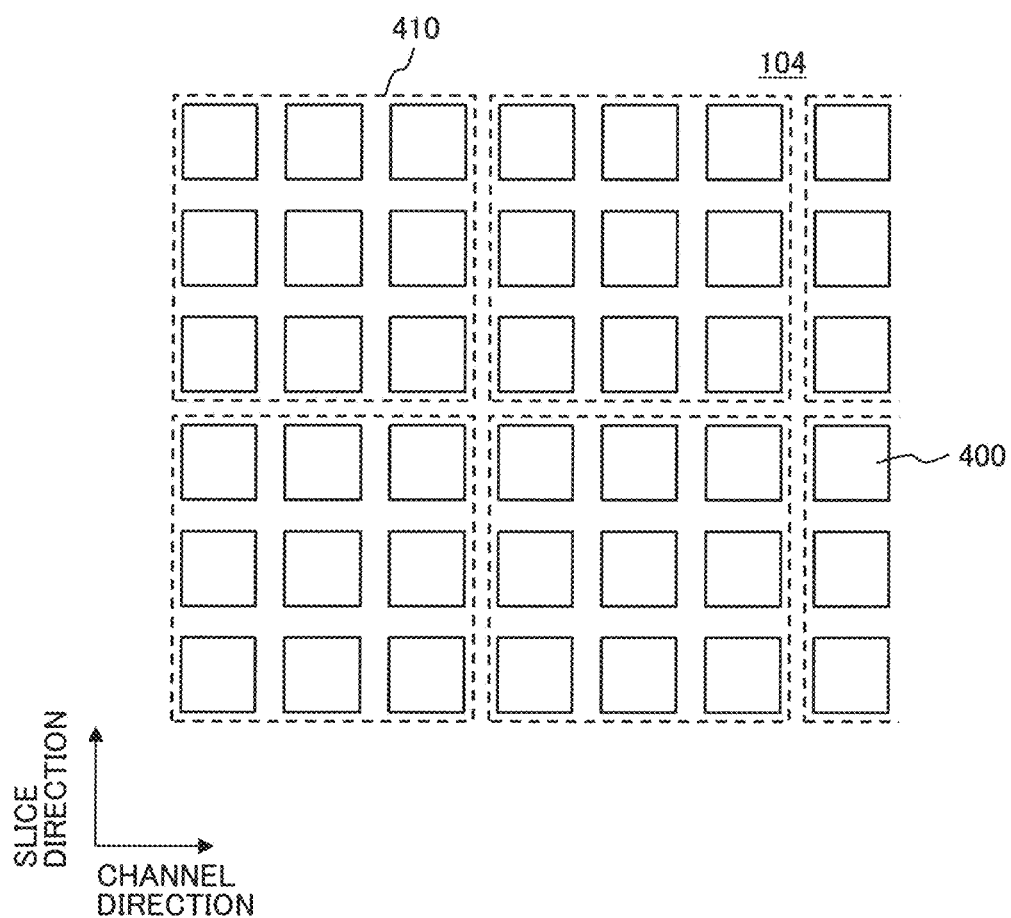
FIG. 2 is a reference diagram illustrating an exemplary array of detection elements in a detection section of the X-ray detector according to the first embodiment of the present invention.

As illustrated, for example, in FIG. 2, the detection section 104 is structured so that a plurality of detection elements 400 (solid line in FIG. 2) of the same size are two-dimensionally disposed in a channel direction and a slice direction and arrayed at equal intervals in both the channel direction and slice direction. The detection elements 400 are disposed with the channel direction coinciding with the rotation direction and with the slice direction coinciding with the rotation-axis direction.

A rectangle enclosed by a broken line in FIG. 2 represents a detection element group (pixel) 410 that is obtained by forming a two-dimensional array of the detection elements 400. The detection element group 410 corresponds to one pixel in a projection image (the detection element group 410 is hereinafter referred to as the pixel 410). In the example illustrated in FIG. 2, the pixel 410 is formed of a total of nine detection elements, namely, three detection elements in the channel direction and three detection elements in the slice direction.

The number of detection elements 400 per pixel is merely an example, and does not limit the present invention.

FIG. 2 illustrates some of the detection elements 400 disposed in the detection section 104. In the example illustrated in FIG. 2, seven detection elements 400 are depicted in the channel direction, and six detection elements 400 are depicted in the slice direction.

A plurality of units of the detection section 104 are disposed in an arc shape and substantially centered around the X-ray source 100, and rotates without changing the positional relationship to the X-ray source 100 when the gantry rotation section 101 rotates. For the sake of explanation, FIG. 1 shows an example in which eight units of the detection section 104 are disposed. In an actual device, however, for example, approximately forty units of the detection section 104 are disposed. An X-ray grid (not shown) is disposed in front of the detection section 104 and used to avoid a situation where X-rays irradiated from the X-ray source 100 and scattered, for example, by the test subject 102 are incident on the detection section 104.

Figure 3:
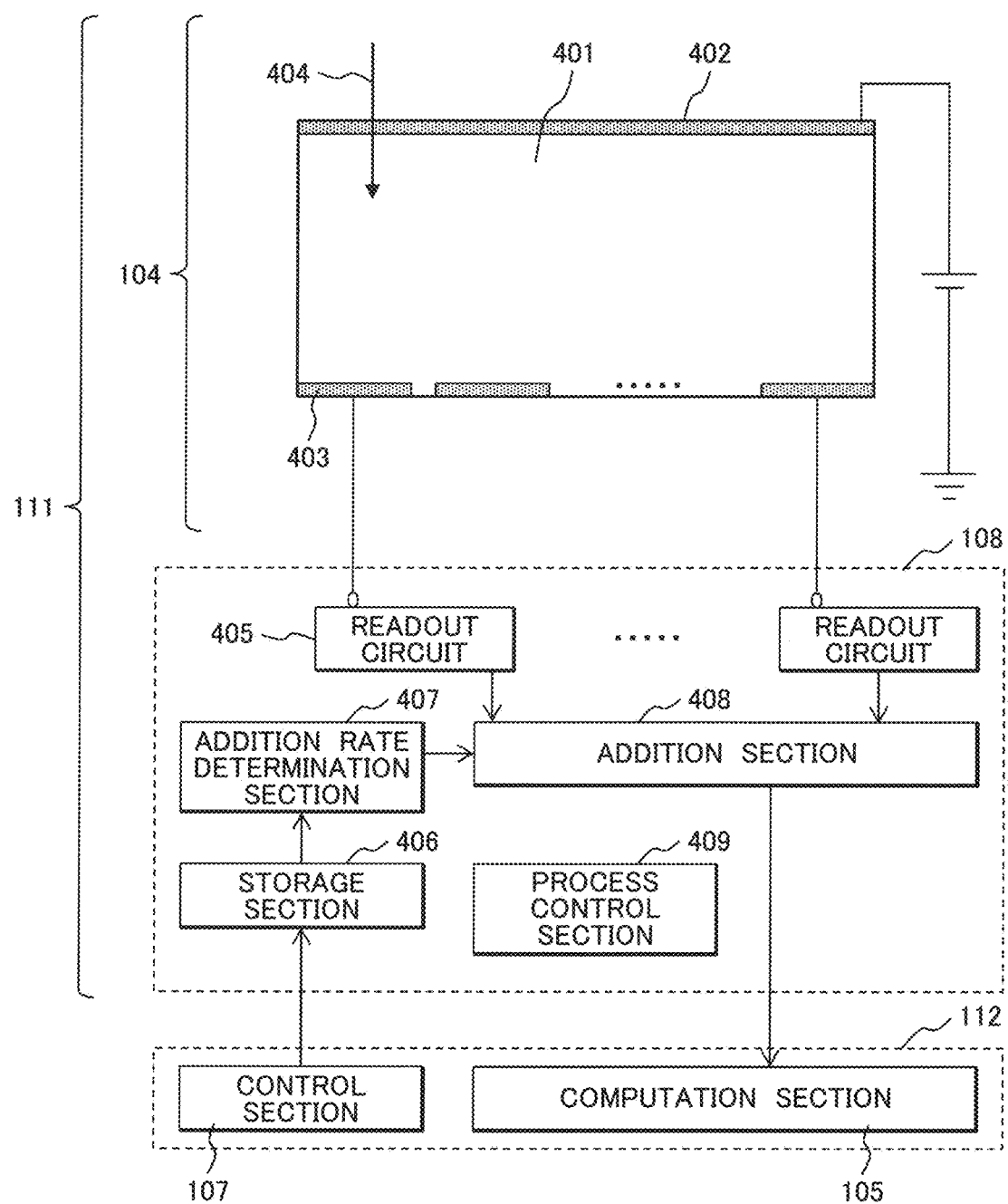
FIG. 3 is a block diagram illustrating an overview of the X-ray detector according to the first embodiment of the present invention.

As illustrated, for example, in FIG. 3, each detection element 400 in the detection section 104 is structured so that a detection layer 401 is sandwiched between a positive electrode 402 and a negative electrode 403, and that a readout circuit 405 is connected to each electrode. In the present embodiment, the positive electrode 402 is a so-called common electrode between the detection elements 400.

The detection layer 401 is formed of semiconductor materials such as CdTe (cadmium telluride), CdZnTe (cadmium zinc telluride), and Si (silicon). X-rays enter the detection layer 401 from the side toward the positive electrode 402 as indicated by an arrow 404. The detection layer 401 then detects X-ray photons and generates an electrical charge whose magnitude corresponds to the photon's energy.

As illustrated in FIG. 3, an analog signal from the detection section 104 is inputted to the signal collection section 108. The signal collection section 108 includes the readout circuit 405, an addition rate determination section 407, a position information storage section 406, an addition section 408, and a process control section 409.

The readout circuit 405 reads out the incidence of X-rays as a trigger, and performs energy separation and digital conversion. The readout circuit 405 generates an electrical signal from an incident electrical charge and separates the electrical signal into a plurality of energy ranges in accordance with a predetermined threshold value. In this instance, the wave height and amount of the generated electrical signal are dependent on the energy of incident X-ray photons, and thus can be separated into energy ranges depending on the X-ray photons. Subsequently, upon receiving the result of separation, the readout circuit 405 acquires a digital signal by digitally counting the number of incident X-ray photons within each energy range.

The above separation method is exercised so that, for example, two energy ranges are discriminated depending on whether they are smaller than a predetermined threshold value (hereinafter referred to as the low energy range) or equal to or greater than the predetermined threshold value (hereinafter referred to as the high energy range). This discrimination is performed upon each sampling so that incident X-ray photons are separated into the high and low energy ranges. The number of X-ray photons in each range is then counted by a digital signal on an individual view basis.

Figure 4:
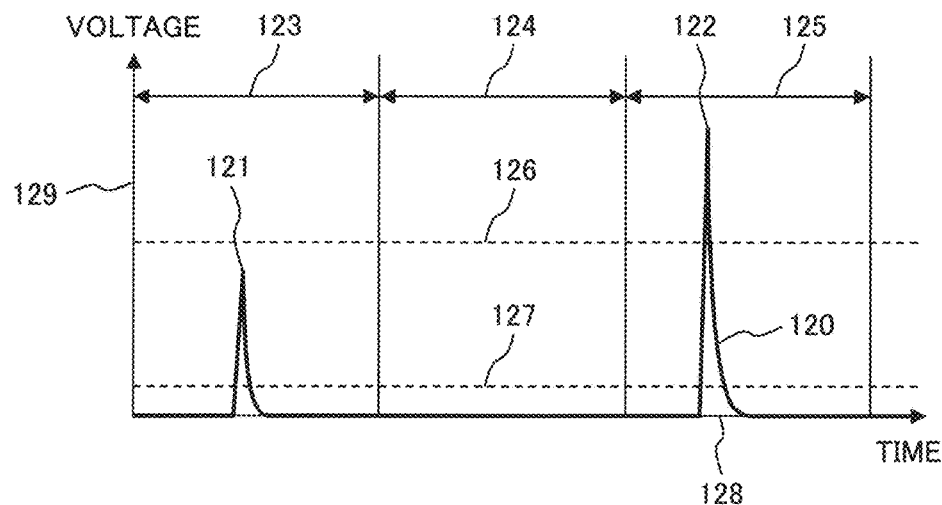
FIG. 4 is a graph illustrating an example of sampling in the X-ray detector according to the first embodiment of the present invention.

An example of the separation method will now be described with reference to FIG. 4. FIG. 4 is a graph illustrating a voltage 120 that is generated from a generated electrical charge. In the graph, the horizontal axis 128 represents time, and the vertical axis 129 represents the voltage. In the example illustrated in FIG. 4, X-rays are incident to generate a pulse output 121 during a sampling time 123, and X-rays are incident to generate a pulse output 122 during a sampling time 125. FIG. 4 illustrates a case where sampling is periodically performed not only at a time point at which X-rays are incident, but also at a time point (a sampling time 124) at which X-rays are not incident. However, sampling may be performed at a time point at which X-ray photons are incident.

Upon each sampling, the readout circuit 405 compares the maximum value of an output voltage during a sampling period with an energy threshold value 126 and an energy threshold value 127 for separation purposes. The energy threshold value 126 is used for separation by determining whether incident X-ray photons are within the high or low energy range. The energy threshold value 127 is used to determine whether X-ray photons are inputted or not. Here, the output voltage 120 varies due to circuit noise of the detection section 104 even when no X-rays are inputted. Therefore, in order to prevent the output voltage 120 from being erroneously detected as a signal generated due to X-rays, the energy threshold value 127 needs to be greater than zero.

As the output voltage 120 is not higher than the energy threshold value 127 during the sampling time 124, for example, in FIG. 4, it is determined by using the above energy threshold values that "no X-ray photons are inputted". Meanwhile, during the sampling time 125, as the output voltage 120 is higher than the energy threshold value 126, it is determined that X-rays within the high energy range are "incident". Further, during the sampling time 123, as the output voltage 120 is higher than the energy threshold value 127 but not higher than the energy threshold value 126, it is determined that X-rays within the low energy range are incident. As described above, the determination of X-ray incidence and the separation into the energy ranges are performed.

Instead of using the maximum value derived from sampling for separation purposes, an integral value of the output voltage during sampling may be used, for instance. The separation method is not limited to the above-described one.

The position information storage section 406 stores pixel position information and defective element position information. The pixel position information indicates the positional relationship between a pixel and the detection elements belonging to a detection element group corresponding to the pixel. The defective element position information indicates the position of a defective element (a detection element having a defect) among a plurality of detection elements in the detection section 104. That is to say, the pixel position information indicates the positions of individual detection elements 400 within a pixel 410, and the defective element position information indicates a detection element group (pixel) 410 to which a defective element belongs, and the position of the defective element within the pixel 410. The pixel position information and the defective element position information can be stored beforehand in the position information storage section 406.

Figure 5:
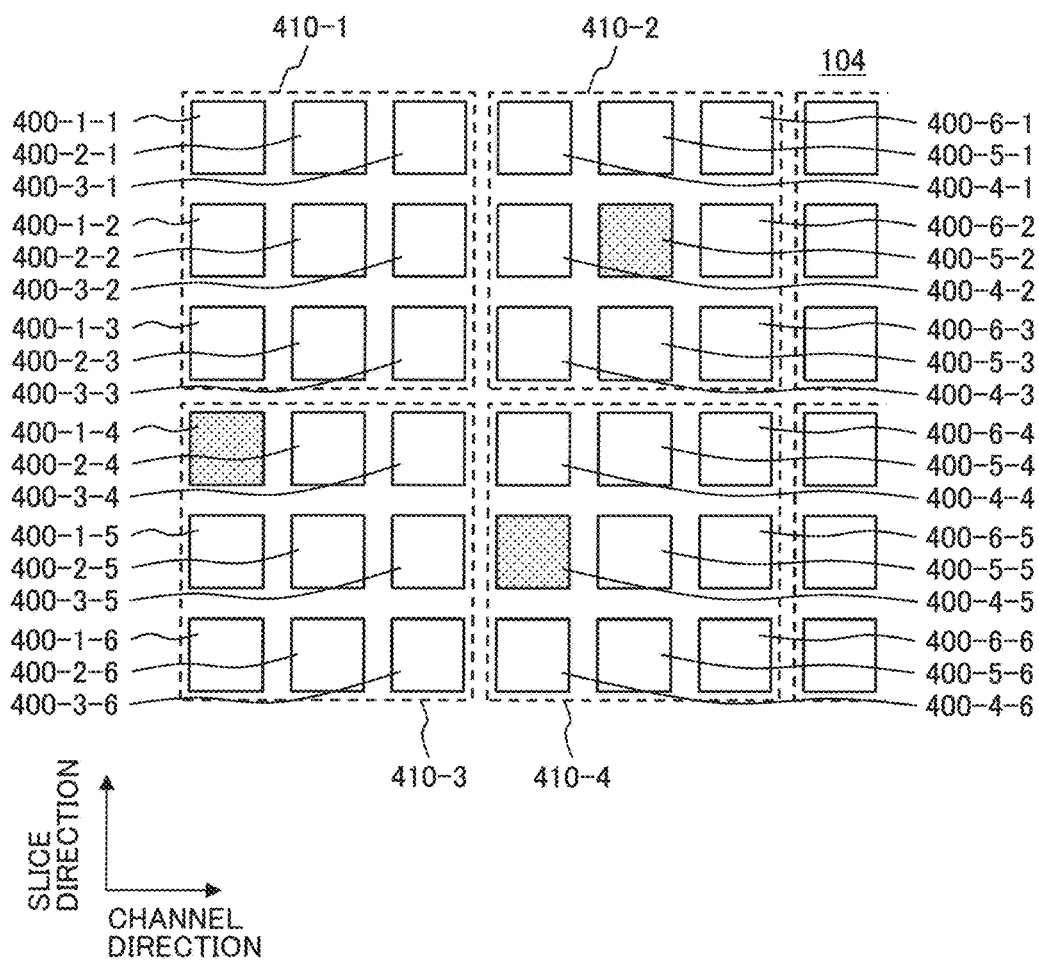
FIG. 5 is a reference diagram illustrating an exemplary array of the detection elements in the detection section of the X-ray detector according to the first embodiment of the present invention.
Figure 6:
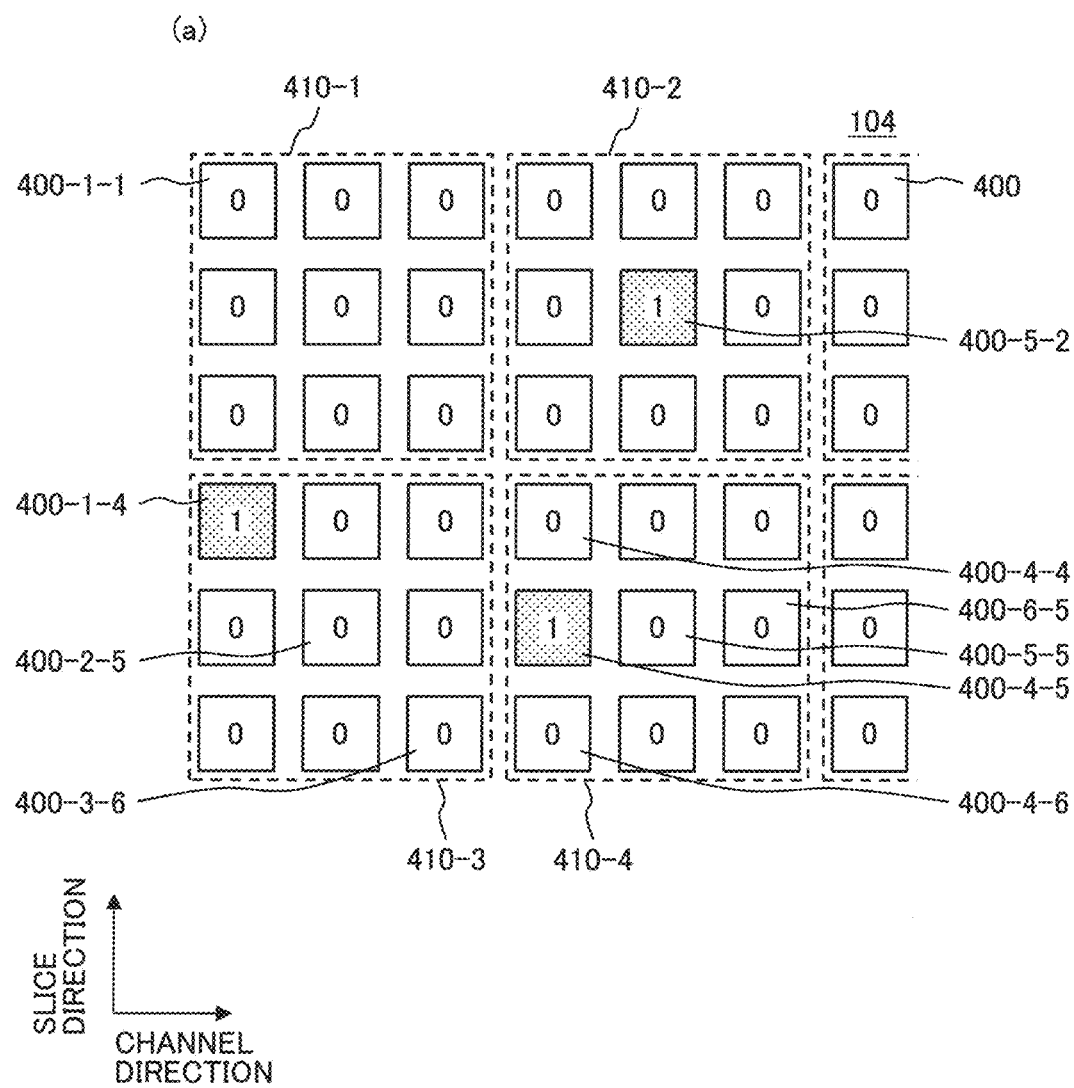
FIG. 6 illustrates an exemplary array of the detection elements in the detection section of the X-ray detector according to the first embodiment of the present invention, (a) illustrates an example of defective element position information indicating the positions of defective elements, and (b) illustrates an exemplary array map of the defective element position information.
Figure 7:
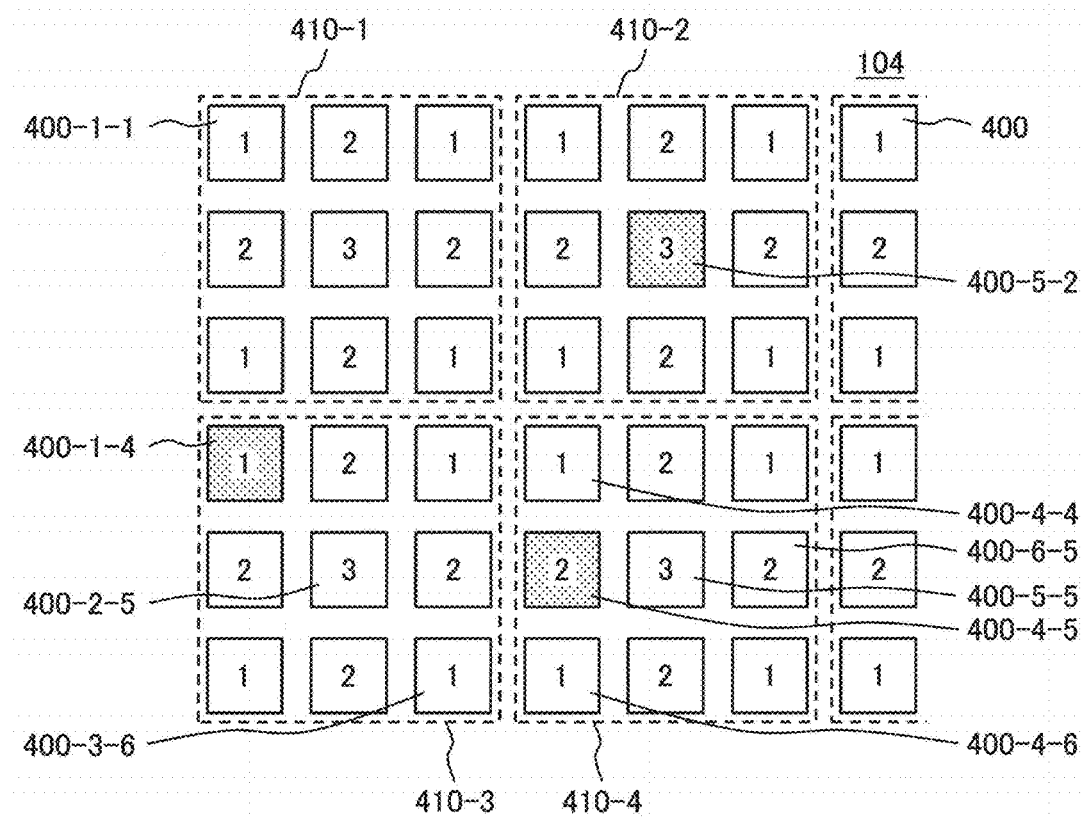
FIG. 7 illustrates an exemplary array of the detection elements in the detection section of the X-ray detector according to the first embodiment of the present invention, (a) illustrates an example of pixel position information indicating the positional relationship between pixels, detection elements, and defective elements, and (b) illustrates an exemplary array map of the pixel position information.

As is the case with FIG. 2, FIGS. 5 to 7 illustrate a part of the detection section 104 to depict the positional relationship between a pixel 410 of a projection image and the detection elements 400. The following description assumes that the detection elements 400-1-4, 400-5-2, 400-4-5 among a plurality of the detection elements shown in FIGS. 5 to 7 are defective elements.

FIG. 6 illustrates an example of the defective element position information stored in the storage section 406. In FIG. 6(a), which shows an array of the detection elements 400 depicted in FIG. 5, normal elements are marked with "0", and defective elements are marked with "1". The storage section 406 stores an array map depicted, for example, in FIG. 6(b) as the defective element position information.

The defective element position information is prepared by irradiating X-rays, for example, without setting a subject, acquiring the outputs from the detection elements 400, comparing the output values with a reference value, and detecting a defective element having an output value smaller than the reference value. As mentioned earlier, the X-ray CT device according to the present embodiment acquires an output value from each energy range. However, an element having an output value smaller than the reference value is determined to be defective. The defective element position information may be prepared automatically by the device or prepared based on a personal determination.

If the outputs of the detection elements 400 are to be obtained without addition, it is necessary to output data by multiplying it by the number of detection elements in a pixel (by nine in the present embodiment). However, an alternative is, for example, to prepare a projection image by allowing the addition section to output only the output value of a selected detection element 400 in a pixel, switch from the selected detection element 400 to another detection element 400, and acquire the projection image of each detection element in the pixel (the projection images of nine detection elements in the present embodiment). However, the defective element position information preparation method and measurement method described here are merely examples. Any information indicative of the positions of defective elements can be applied.

FIG. 7 illustrates an example of pixel position information. In FIG. 7(a), which shows an array of the detection elements 400 depicted in FIG. 5, a detection element at the center of a pixel is marked with "3", a detection element at a corner is marked with "1", and other detection elements are marked with "2".

The storage section 406 stores an array map depicted, for example, in FIG. 7(b) as the pixel position information. Such pixel position information is merely an example. An alternative is, for example, to store the position information about a relevant detection element 400 as coordinate information on an individual position basis. Further, if coordinates are periodic, the pixel position information may be stored in the form, for example, of a numerical formula. Moreover, the central position of a pixel may be given in the form, for example, of coordinates or a numerical formula.

Based on the defective element position information and pixel position information stored in the position information storage section 406, the addition rate determination section 407 determines the addition rate for each detection element 400 belonging to a pixel 410. More specifically, based on the defective element position information and pixel position information, the addition rate determination section 407 determines the addition rate for an output signal from a defective element included in a pixel 410 targeted for signal value calculation and the addition rate for an output signal from a detection element positioned symmetrically with respect to the defective element about the center of the pixel 410 targeted for signal value calculation in such a manner that the addition rates are equal and lower than the addition rates for the other detection elements, and determines the addition rates for the other detection elements in such a manner that they are substantially equal.

Here, the addition rate is a numerical value of 0 or greater. An addition rate of 1 is for a case where all output signals are to be used. An addition rate of 0 is for a case where no output signals are to be used. If, for example, no output signals of defective elements are to be used, the addition rate should be set to 0. If all output signals of normal detection elements are to be used, the addition rate should be set to 1. A procedure for determining the addition rate, concrete examples of the addition rate, and an output value calculation method for each pixel will be described later.

In accordance with the addition rate determined by the addition rate determination section 407, the addition section 408 calculates the output value of a pixel 410, as an output value for each pixel of a projection image, by performing weighted addition of the output signals of individual detection elements 400 belonging to the pixel 410. In the present embodiment, the pixel 410 is formed, for example, a total of nine detection elements 400, namely, three elements in the channel direction and three elements in the slice direction (see FIG. 2). Therefore, the addition section 408 calculates the output value of the pixel 410 by performing weighted addition of the output signals of the nine detection elements 400.

When, for example, the output value of the pixel 410 is $R_{cell}$, the outputs of the detection elements 400-$i$-$j$ in the pixel 410 (i and j are integers of 1 to 3) are $r(i, j)$, and the addition rate, which is the weight for them, is $\alpha(i, j)$, the weighted addition can be performed by using Equation (1) below.

$$R_{cell} = \sum_{i=1}^{M} \sum_{j=1}^{N} \alpha(i,j) r(i,j) \qquad \text{Equation (1)}$$

In Equation (1), M (M is a natural number) represents the number of detection elements in the channel direction within one pixel, and N (N is a natural number) represents the number of detection elements in the slice direction within one pixel. In the present embodiment, M and N are both 3.

The output values of the other pixels are similarly calculated by performing weighted addition, at the addition rate, of the output values of the detection elements 400 in the other pixels. The weighted addition is performed for each energy range.

The process control section 409 controls individual sections included in the signal collection section 108 in order to perform the above-described process. The output value of the pixel 410, which is calculated by the signal collection section 108, is outputted to the computation section 105 as a projection image.

Based on the above-described configuration, a general imaging operation of the X-ray CT device will now be described. For the sake of explanation, the following description assumes that two photon energy ranges are provided. Alternatively, however, three or more photon energy ranges may be provided.

First of all, when imaging personnel inputs imaging conditions from the input section 110 to start an actual imaging sequence, the control section 107 starts an imaging operation by controlling the irradiation of X-rays from the X-ray source 100 and controlling the gantry rotation section 101.

In the above instance, an electron beam is accelerated at a tube voltage, for example, of 120 kV to let the X-ray source 100 irradiate X-rays. The X-rays irradiated from the focal point of the X-ray source 100 are incident on a test subject 300 on the bed top plate 103, and the X-rays transmitted through the test subject 300 are detected by the detection section 104. For each detection element 400, the detection section 104 generates an electrical charge corresponding to the energy of the incident X-rays. The signal collection section 108 separates the electrical charge into the high and low energy ranges as mentioned earlier, and obtains a digital count value of each energy range and each view. Further, the signal collection section 108 determines the output value of each pixel of a projection image, and outputs the determined output value to the computation section 105.

Next, the control section 107 controls the above-described imaging operation by rotating the gantry rotation section 101 in the direction of rotation as needed to vary the angle of X-ray irradiation toward the test subject 300. For this view, a measurement is made in the same manner as for the previous view, and the result of measurement is outputted as the count value of each energy range. Here, the X-rays generated from the X-ray source 100 may be pulsed X-rays synchronized with a view or continuous X-rays. Further, while the gantry rotation section 101 is rotationally driven as described above, the imaging operation is repeatedly performed with the focal point changed for each view in order to acquire 360-degree digital signals. The imaging operation is performed, for example, at 0.4-degree intervals for a plurality of views. The imaging operation is performed in this manner to obtain a 360-degree projection image.

Next, the computation section 105 prepares a multi-energy projection image by performing a predetermined correction process and computation process on the projection image collected by the signal collection section 108. The correction process provides, for example, air correction. The computation process provides, for example, density image creation, projection image preparation for a multi-energy image, and reconfiguration.

An example of an addition method used in the addition section 408 will now be described with reference to the flowchart of FIG. 8.

Figure 8:
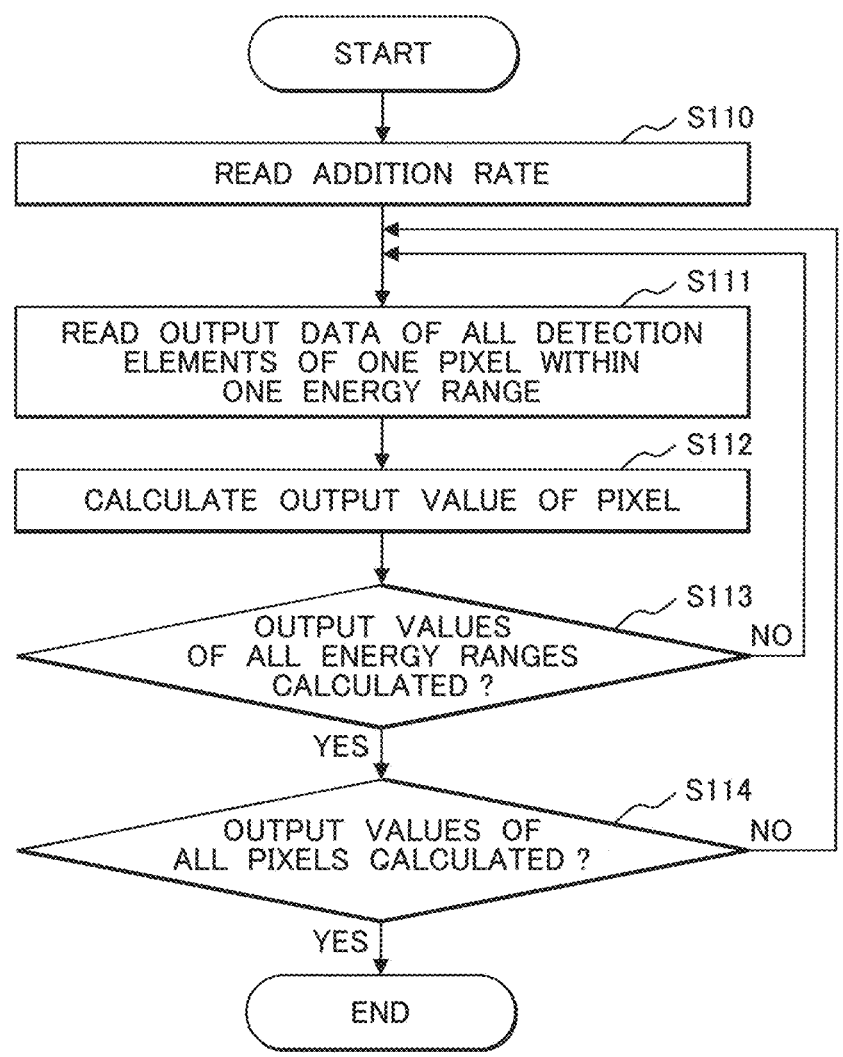
FIG. 8 is a flowchart illustrating an addition process in an addition section of the X-ray detector according to the first embodiment of the present invention.

As illustrated in FIG. 8, first of all, in step S110, the addition section 408 reads the addition rate, which is determined by the addition rate determination section 407 before an imaging operation. This step is performed, for example, when the system starts up or before an actual imaging operation is started in response to an input instruction for the start of imaging.

When an actual imaging operation starts, in step S111, the addition section 408 acquires the outputs of all detection elements of a pixel within one energy range from the readout circuit 405. Next, in step S112, the addition section 408 determines the output value of one pixel within one energy range from the addition rate and the output values of detection elements, and transfers the result of determination to the computation section 105 in the signal processing section 112.

Next, in step S113, the addition section 408 determines whether the output values of all energy ranges are calculated. If a NO determination result is obtained, processing returns to step S111. In step S111, the readout circuit 405 is accessed to obtain the output of an energy range that relates to the detection elements of the same pixel and has not been subjected to step S112. If, by contrast, a YES determination result is obtained in step S113, processing proceeds to the next step, that is, step S114. In step S114, a check is performed to determine whether the output values of all pixels are calculated.

If a NO determination result is obtained in step S114, processing returns to step S111. In step S111, the same process is performed to read the outputs of all energy ranges. If, by contrast, a YES determination result is obtained in step S114, processing terminates.

The above-described addition method is merely an example. An alternative is, for example, to change the order of processing steps of the addition method or collectively perform a read operation and a computation operation on a plurality of sets of data. Further, a process of the same generation can be performed on different data units. Moreover, instead of transferring the output values of individual pixels to the signal processing section 112 one after another, the addition section 408 may collectively transfer the output values to the signal processing section 112 after acquiring data on all energy ranges of all pixels.

The following describes the relationship between the addition rate $\alpha(i, j)$ and SNR in a situation where the output signals of detection elements are subjected to weighted addition to obtain the output value of each pixel.

When all the SNRs of the output signals of the detection elements 400-$i$-$j$ (marked with $snr(i, j)$) are identical with each other and regarded as the SNR of the output value of a pixel after weighted addition (marked with $SNR_{cell}$), Equation (2) below, which expresses the relationship, is obtained from Equation (1).

$$SNR_{cell} = \frac{\sum_{i=1}^{M}\sum_{j=1}^{N} \alpha(i, j)}{\sqrt{\sum_{i=1}^{M}\sum_{j=1}^{N} \alpha^2(i, j)}} snr(i, j) \qquad \text{Equation (2)}$$

(Notes on an Addition Rate Determination Method)

A weighting (addition rate) determination method used in the addition rate determination section 407 will now be described in detail. The addition rate determination method varies depending on the presence and position of a defective element.

It is assumed that when there are no defective elements as in a pixel 410-1 in FIG. 5, the addition rate for all detection elements 400 is 1. Meanwhile, when there is a defective element as in the pixel 410-2, the pixel 410-3, and the pixel 410-4, the addition rate determination section 407 decreases the addition rate for normal elements by one and sets an addition rate of 0 for the defective element.

However, if weighted synthesis is performed by using the above-described addition rate as is, the output value sampling position of a pixel is shifted from the center of the pixel. More specifically, if an addition rate of 0 is applied, for example, to the pixel 410-4, which has a defective element 400-4-5, the sampling position is shifted in the channel direction by ⅑ of the detection elements 400 and by 1/27 of the pixel. It should be noted, however, that such values prevail when there is no gap between the detection elements.

If the sampling position is shifted, the following influence is exerted. For example, the output of one pixel may be approximately three times higher than the output of a neighboring pixel in the vicinity, for example, an edge of the subject. When such a difference is assumed to be exponential, the outputs differ by approximately 4% if the sampling position is shifted by ⅑ of the detection elements 400 (1/27 of a pixel). Such a shift causes an artifact particularly in an X-ray CT device.

Consequently, the addition rate determination section 407 sets the addition rate for a defective element to 0, and changes the other addition rates in such a manner that the sampling position is at the center of a pixel, and that the center of gravity of addition rates in the pixel is centered.

The center of gravity of the addition rates is determined by standardizing, with the number of detection elements 400, the sum of products of the addition rates for the detection elements 400 and the vectors between a start point and the center of the detection elements 400. More specifically, when a pixel is formed of N detection elements (N is an integer of 2 or greater), the vector between the start point and a detection element k (k is an integer of 1 to N) is d(k), and the addition rate for that detection element 400 is a(k), the center of gravity G of the addition rates can be expressed by Equation (3).

$$G = \frac{1}{N}\sum_{k=1}^{N} \alpha(k)d(k) \quad \text{Equation (3)}$$

When the start point of the vector is at the center of a pixel, that is, the start point coincides with the center of the pixel, the center of gravity of the addition rates is zero vector. The following description assumes that the start point is at the center of a pixel.

Figure 9:
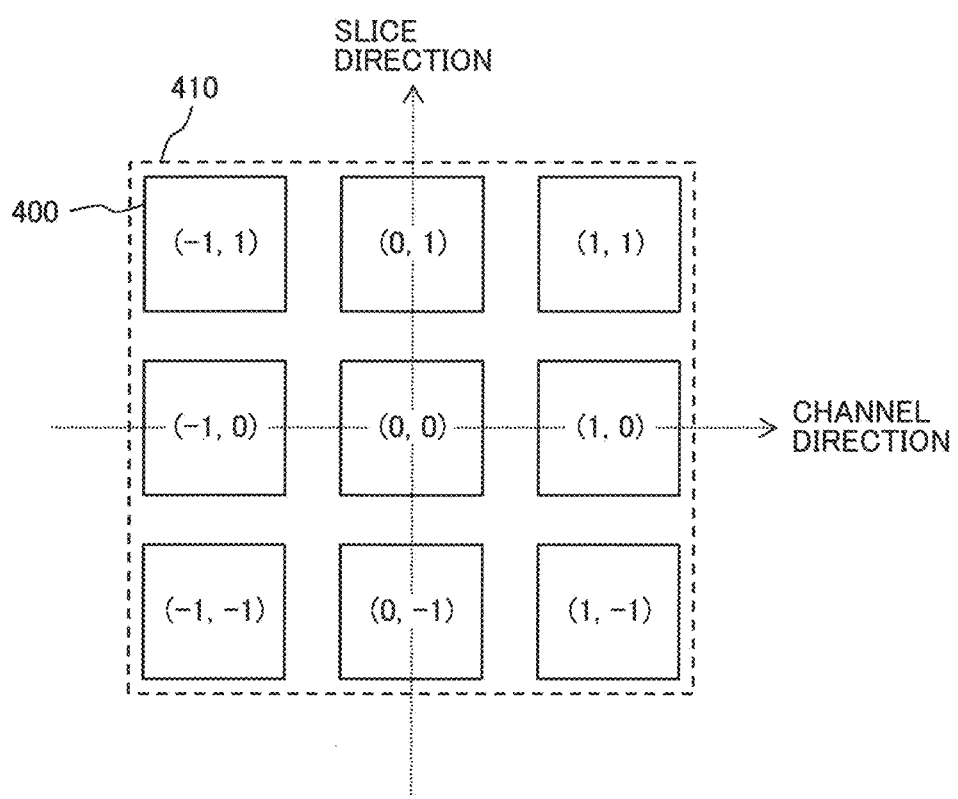
FIG. 9 is a diagram illustrating an exemplary array of the detection elements in the detection section of the X-ray detector according to the first embodiment of the present invention and, in particular, the center of gravity of an addition rate.

The center of gravity of addition rates will now be described in detail with reference to FIG. 9. FIG. 9 illustrates nine detection elements 400 in one pixel, and (i, j) (i and j are integers of −1, 0, and 1) are coordinates prevailing when the center of the pixel is the origin and the length between the detection elements 400 is a unit length. Further, i represents the channel direction, and j represents the slice direction. When the addition rates for individual detection elements 400 are α(i, j), the channel direction coordinate of the center of gravity of the addition rates is x, and the slice direction coordinate of the center of gravity of the addition rates is y, Equations (4-1) and (4-2) below (hereinafter collectively referred to as Equations (4)), which respectively express the coordinates (x, y), are obtained from Equation (3).

$$x = \frac{-(\alpha(-1,-1) + \alpha(-1,0) + \alpha(-1,1)) + (\alpha(1,-1) + \alpha(1,0) + \alpha(1,1))}{9} \quad \text{Equation (4-1)}$$

$$y = \frac{-(\alpha(-1,-1) + \alpha(0,-1) + \alpha(1,-1)) + (\alpha(-1,1) + \alpha(0,1) + \alpha(1,1))}{9} \quad \text{Equation (4-2)}$$

All detection elements 400 in the above pixel 410-1 are normal so that the addition rates are 1. Therefore, the center of gravity (x, y) of the addition rates is (0, 0) and thus obviously identical with the center of the pixel.

Next, if there is a defective element, the addition rate determination section 407 identifies the position of the defective element within the pixel and determines the addition rates in accordance with the positions of the detection elements 400 in the pixel. The position of the defective element within the pixel is identified based on the defective element position information and pixel position information stored in the storage section 406.

More specifically, a defective element is marked with "1" according to the defective element position information, for example, in FIG. 6. It indicates that the defective element 400-5-2 is in the pixel 410-2. This further reveals that this detection element 400 is indicated by the numeral 3 within the pixel position information in FIG. 10, and positioned at the center of the pixel as is obvious from the aforementioned definition.

Figure 10:
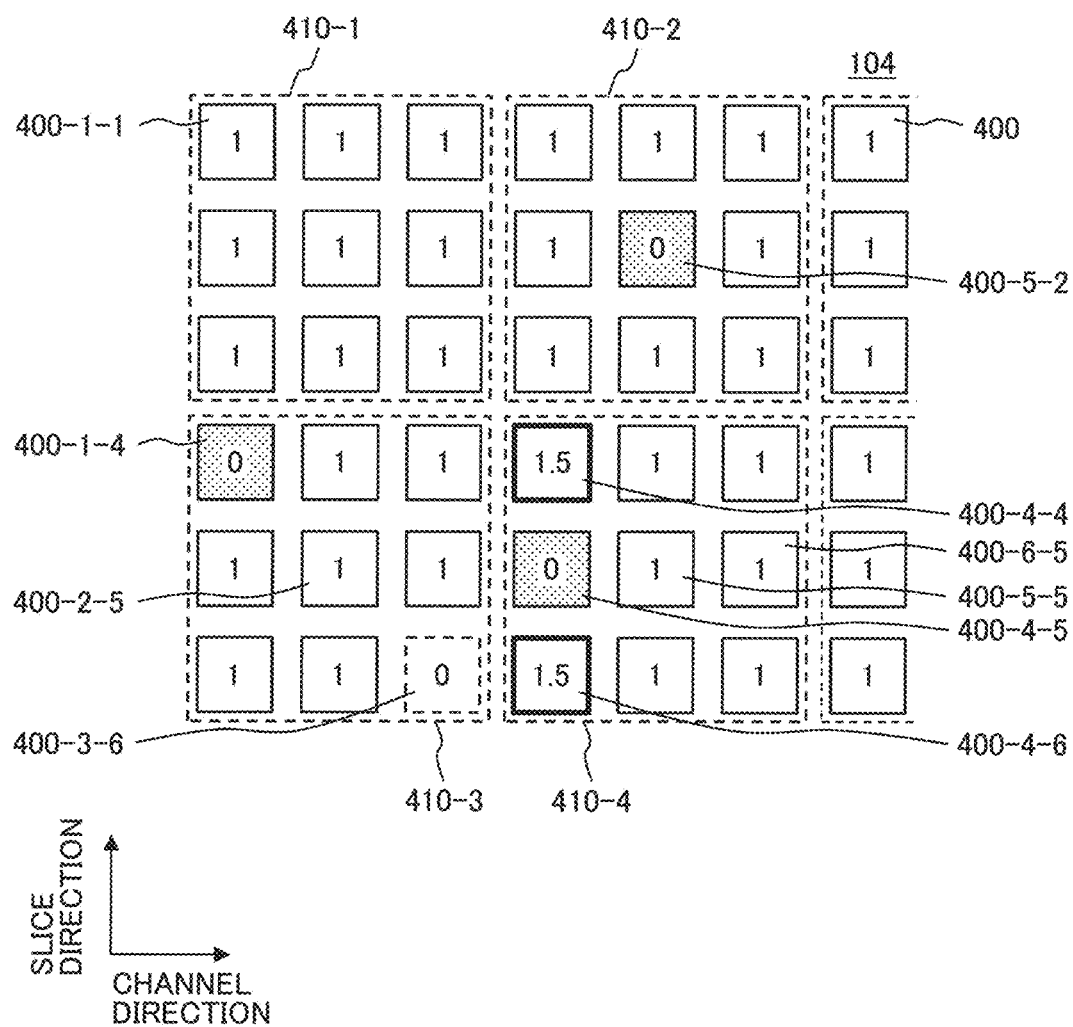
FIG. 10 is a diagram illustrating an exemplary array of the detection elements in the detection section of the X-ray detector according to the first embodiment of the present invention and, in particular, the addition rate for the detection elements.

A case where addition rate determination is based on the position of a defective element will now be described with reference to FIG. 10. Numerals marked in the detection elements 400 shown in FIG. 10 represent the addition rates for the individual detection elements 400 in a case where there is a defective element. Further, the following assumes that the amount decreased from an addition rate of 1 for a normal detection element is defined as the addition rate decrease amount. That is to say, if, for example, the addition rate for a defective element is 0, the addition rate decrease amount is 1. Similarly, the amount increased from an addition rate of 1 for a normal detection element is defined as the addition rate increase amount.

(When a Defective Element is at a Corner of a Pixel)

In this case, the detection element 400-1-4 in the pixel 410-3 shown, for example, in FIG. 6(a) is defective and positioned at a corner of the pixel 410-3. This corresponds to a case where (−1, 1) in FIG. 9 is a defective element. Therefore, when only the addition rate for the defective element 400-1-4 is 0, that is, the addition rate decrease amount is 1, the center of gravity (x, y) of the addition rates is (⅑, −⅑) and not at the center of the pixel.

In order to position the center of gravity of the addition rates at the center of the pixel, the addition rate determination section 407, then, as illustrated in FIG. 10, similarly sets the addition rate decrease amount to 1 and thus sets the addition rate for a detection element 400-3-6 (indicated by a broken line in FIG. 10) to 0. The detection element 400-3-6 is a diagonal detection element that is positioned symmetrically with respect to the defective element 400-1-4 in the pixel about the center of the pixel (detection element 400-2-5 in FIG. 10).

That is to say, the addition rate decrease amount for the diagonal detection element is equalized with the addition rate decrease amount for the defective element 400-1-4. When the addition rates are determined as described above, the center of gravity (x, y) of the addition rates is (0, 0) and thus identical with the center of the pixel.

The above-described method is superior in SNR to a method based on so-called extrapolation. FIG. 11(*a*) indicates the addition rates within a pixel when (−1, 1) in FIG. 9 is a defective element and the addition rate for the defective element is set to 0. FIG. 11(*b*) indicates the addition rates within the pixel when the addition rates for the defective element (−1, 1) and its diagonal detection element (1, −1) are set to 0. When the addition rates are set as described above, the SNR is lowered by 5.7% in the case of FIG. 11(*a*) and by 11.8% in the case of FIG. 11(*b*) as compared to a case where there are no defective elements and the addition rates for all detection elements 400 are 1.

Meanwhile, in the case of addition rates obtained by extrapolation as indicated in FIGS. 11(*c*) to 11(*f*), the degree of SNR decrease is as described below. FIG. 11(*c*) indicates addition rates that are obtained by estimating, in a diagonal direction, the output value of a defective element (−1, 1) by extrapolation through the use of the output values of detection elements 400 at (0, 0) and (1, −1). These resulting addition rates are understandable because, when the output value P(−1, 1) of a detection element (−1, 1) is to be estimated from the output value P(0, 0) of a detection element (0, 0) and the output value P(1, −1) of a detection element (1, −1), the output value P(−1, 1) can be expressed by Equation (5) below and it is necessary to increase the addition rate for (0, 0) by 2 and decrease the addition rate for (1, −1) by 1. Further, even when extrapolation is performed, the addition rate for the diagonal detection element is the same 0 as the addition rate for the defective element so that the center of gravity of the addition rates is identical with the center of the pixel.

$$P(-1,1)=2P(0,0)-P(1,-1) \quad \text{Equation (5)}$$

When the addition rates are as indicated in FIG. 11(*c*), the SNR is decreased by approximately 22.5% as compared to a case where there are no defective elements and the addition rates for all detection elements 400 are 1. The rate of SNR decrease can be determined from Equation (2).

Similarly, FIG. 11(*d*) indicates addition rates that are obtained when the output value of (−1, 1) is determined by extrapolation through the use of detection elements 400 at (0, 1) and (1, 1) in the same row. FIG. 11(*e*) indicates addition rates that are obtained when the output value of (−1, 1) is determined by extrapolation through the use of detection elements 400 at (−1, 1) and (−1, −1) in the same column. In these cases, too, the SNR is decreased by approximately 22.5% as compared to a case where there are no defective elements and the addition rates for all detection elements 400 are 1, as is the case with FIG. 11(*b*).

Similarly, FIG. 11(*f*) indicates addition rates that are obtained when the output value of a defective element is determined by performing extrapolation on the same row, on the same column, and on a diagonal and adding ⅓ of the explanation results together. In this instance, the addition rates for (1, 1), (1, −1), and (−1, −1) are decreased by ⅓ to ⅔, and the addition rates for (0, 1), (0, 0), and (1, 0) are increased by ⅔ to 5/3. In this case, the SNR is decreased by 12.2% as compared to a case where there are no defective elements and the addition rates for all detection elements 400 are 1.

When the above-described addition rates determined by the addition rate determination section 407 of the X-ray detector according to the present embodiment are used to perform weighted addition in order to calculate the output value on an individual pixel basis, it is possible to suppress a decrease in the SNR for a pixel output value as compared to a case where the addition rates determined by so-called extrapolation are applied.

That is to say, the decrease in the SNR can be best suppressed when the addition rates for detection elements 400 other than a defective element and its diagonal detection element are equal. As described above, the addition rate determination section 407 according to the present embodiment decreases the addition rates for a defective element and its diagonal detection element by the same value from the addition rates for normal detection elements, and sets substantially equal addition rates for the other detection elements 400, that is, sets the addition rates for the other detection elements 400 in a substantially uniform manner. As a result, the center of gravity of the addition rates becomes identical with the center of a pixel, thereby suppressing a decrease in the SNR. Substantially equal addition rates, that is, addition rates set in a substantially uniform manner, denote that, for example, the difference in addition rates is not greater than approximately ±10%.

(When a Defective Element is Neither at a Corner of a Pixel Nor at the Center of the Pixel)

A case where, for example, the detection element 400-4-5 is defective as in the pixel 410-4 shown in FIG. 6(*a*) corresponds to a case where a detection element at (−1, 0) in FIG. 9 is defective.

If only the addition rate for the defective element 400-4-5 in the above-described pixel is set to 0, that is, the addition rate decrease amount is set to 1, the center of gravity (x, y) of the addition rates is (⅕, 0) so that the center of gravity of the addition rates is not identical with the center of the pixel.

Consequently, the addition rates for elements around the defective element 400-4-5 are increased. As illustrated in FIG. 10, the present embodiment increases the addition rates for detection elements 400-4-4 and 400-4-6 (detection elements marked by thick solid lines) by only 0.5. More specifically, the addition rates for the detection element 400-4-4 and the detection element 400-4-6 are set to 1.5 (i.e., an addition rate increase amount of 0.5), the addition rate for the defective element 400-4-5 is set to 0 (i.e., an addition rate decrease amount of 1), and the addition rates for the other detection elements 400 are set to 1.

The above case corresponds to a case where the output signal of the detection element 400-4-5 is obtained by performing interpolation on the output signals of the detection element 400-4-4 and detection element 400-4-6. When the addition rates are determined in the above manner, the center of gravity (x, y) of the addition rates is (0, 0) and thus identical with the center of the pixel.

(When a Defective Pixel is at the Center of a Pixel)

When, for example, the detection element 400-5-2 is defective as in the pixel 410-3 shown in FIG. 6(*a*), the center of gravity (x, y) of the addition rates is (0, 0) and the central detection element is defective. Therefore, only the addition rate for the defective element 400-4-5 is set to 0, and the addition rates for the other detection elements 400 are allowed to remain unchanged without being decreased.

When the addition rates are set as indicated in the above example, the output value of each pixel can be calculated in such a manner that the sampling position for a projection image pixel 410 does not shift from its actual position.

The above-described addition rate determination process for each detection element is basically performed in a manner described below.

First of all, (1) the addition rates for all detection elements are set to 1, and the addition rate for each defective element is decreased by 1. Next, (2) the position of the defective element is checked based on the defective element position information in order to determine whether the defective element is at a corner of a pixel, at the center of the pixel, or at some other position. Subsequently, (3) if the position of the defective element is at a corner of the pixel, the position of a diagonal detection element is determined, and if the diagonal detection element is not defective, its addition rate is decreased by 1. If the position of the defective element is neither at a corner of the pixel nor at the center of the pixel, the addition rates for elements surrounding the defective element are increased in such a manner that the output of the defective element is interpolated by the surrounding elements in the same pixel. However, if, for example, the surrounding elements are defective, the outputs of the defective elements may not always be interpolated by the surrounding elements. In such an instance, the addition rate for the diagonal detection element is decreased by 1 without increasing the addition rates for the elements surrounding the defective elements.

If there are a plurality of defective elements, the addition rates can be determined by repeating processing steps (2) and (3) above for all defective elements.

The above example assumes that an addition rate decrease amount of 1 is set for a defective element and for a diagonal detection element in a case where the defective element is at a corner of a pixel. However, an addition rate decrease amount of greater than 0 and smaller than 1 may alternatively be set. In such a case, too, the same addition rate decrease amount is set for the diagonal detection element and the defective element.

The addition rate determination process in the addition rate determination section 407 will now be described in more detail with reference to the flowchart of FIG. 12.

First of all, for purposes of addition rate determination, the addition rate determination section 407 sets, in step S200, the addition rates for all detection elements to 1, and then proceeds to step S201 and decreases the addition rates for all defective elements by 1. In this instance, whether a detection element is defective is determined based on the defective element position information stored in the storage section 406, that is, based, for example, on the array map shown in FIG. 6.

Next, in step S202, a check is performed to determine the position of a defective element in a pixel. This determination is made based on the defective element position information and pixel position information stored in the storage section 406, that is, by using the array map shown, for example, in FIGS. 6 and 7. If the result of determination of the position of the defective element indicates that the defective element is at a corner of the pixel, processing proceeds to step S203. If the defective element is positioned neither at the center of the pixel nor at a corner of the pixel, processing proceeds to step S205. If the defective element is positioned at the center of the pixel, processing proceeds to step S209.

In step S203, a check is performed to determine whether a diagonal detection element relative to the defective element is defective. If the diagonal detection element is not defective, processing proceeds to step S204. In step S204, the addition rate for the diagonal detection element relative to the defective element is decreased by 1. Upon completion of step S204, processing proceeds to step S209. If, by contrast, it is determined in step S203 that the diagonal detection element is defective, processing proceeds to step S209.

If it is determined in step S202 that the defective element is positioned neither at the center of the pixel nor at a corner of the pixel, addition rate determination is made by checking whether the output of the defective element can be interpolated by the surrounding elements. More specifically, a check is performed in step S205 to determine whether detection elements are positioned above and below the defective element and nondefective. If a YES determination result is obtained, that is, normal detection elements are in the same pixel as the defective element and positioned above and below the defective element, processing proceeds to step S206. In step S206, the addition rates for the detection elements above and below the defective element are increased by 0.5.

If, on the contrary, a NO determination result is obtained in step S205, that is, normal detection elements are in the same pixel as the defective element and positioned neither above nor below the defective element, processing proceeds to step S207. In step S207, a check is performed to determine whether detection elements in the same pixel as the defective element are positioned to the left and right of the defective element and both normal.

If a YES result is obtained in step S207, that is, detection elements in the same pixel as the defective element are positioned to the left and right of the defective element and both normal, processing proceeds to step S208. In step S208, the addition rates for the detection elements positioned to the left and right of the defective element are increased by 0.5. If, on the contrary, a NO result is obtained, that is, detection elements in the same pixel as the defective element and positioned to the left and right of the defective elements are both abnormal, processing proceeds to step S204. In step S204, the addition rate for a diagonal detection element relative to the defective element is decreased by 1.

When the above-described process is performed and detection elements above and below the defective element are normal, the result is the same as when the output of the defective element is determined by performing interpolation on the outputs of such normal elements. If at least one of the detection elements positioned above and below the defective element is abnormal, the result is the same as when the output of the defective element is determined by interpolation on the left and right detection elements. If at least one of the left and right detection elements is a defective element, the addition rate for a diagonal detection element is decreased by 1, as is the case where the defective element is positioned at a corner of the pixel.

Next, in step S209, a check is performed to determine whether the position determination in step S202 is made for all defective elements. If not, processing returns to step S202, and steps S202 to S208 are performed similarly for the next defective element whose position has not been determined.

When the above-described process is performed on all defective elements, the addition rate determination process terminates. The above-described process is able to determine the addition rates for all detection elements even if there are a plurality of defective elements.

The above-described method of increasing the addition rates for detection elements adjacent to a defective element, that is, the method of determining whether the output of a defective element can be interpolated by the surrounding elements, is merely an example. Specifically, determination may be made in such a manner that the center of gravity of the addition rate increase amounts used for the surrounding elements is identical with the center of the defective element. For example, an alternative is to change the order of determinations to be made in steps S205 and S207, determine whether interpolation can be performed with three or more surrounding elements, or use surrounding elements other than those positioned above, below, or to the left or right of a defective element.

When the addition rate determination section 407 determines the addition rates as described above, it is possible to inhibit an element made defective due, for instance, to a defect from shifting the sampling position of a projection image pixel and thus altering the output value. This further makes it possible to easily avoid or reduce the occurrence of artifacts and obtain an accurate output value.

Meanwhile, if the addition rates for a defective element and detection elements 400 positioned symmetrically with respect to the defective element about the center of the pixel are decreased as described above, the output value of the pixel including the defective element decreases. Therefore, it is necessary to standardize the total addition rate for pixels so that the addition rates for individual pixels are uniform. Consequently, for example, a standardization section is incorporated in the addition section 408 and allowed to determine the addition rates for output signals of detection elements included in each pixel and then standardize the addition rate difference between the pixels.

More specifically, standardization may be performed, for example, with the sum of addition rates for the detection elements included in a pixel. That is to say, as the sum of the addition rates for the pixel 410-1 shown, for example, in FIG. 10 is 9, the addition section 408 calculates the output value by the addition method indicated by Equation (1) and then allows the standardization section to divide the output value by 9, which is the sum of the calculation rates. Similarly, for example, as the sum of the addition rates for the pixel 410-2 is 8, the standardization section divides the output value by 8, which is the sum of the calculation rates. As described above, the standardization section is able to compensate for the difference between the output values of pixels, which is caused by the difference between the pixels in the number of detection elements used, by standardizing the pixel output values determined by the addition section 408, that is, a projection image.

An alternative, for example, is to, instead of incorporating the standardization section, allow the addition rate determination section 407 to predetermine the addition rate for each detection element in such a manner that the sum of addition rates for all pixels is 1. More specifically, referring, for example, to FIG. 10, the value ⅑ can be obtained by dividing the addition rates for individual detection elements included in the pixel 410-1 by 9, which is the sum of addition rates for the pixel 410-1, and the value ⅛ can be obtained by dividing the addition rates for individual detection elements included in the pixel 410-2 by 8, which is the sum of addition rates for the pixel 410-2.

Another alternative is to allow the correction processing section 1052 in the computation section 105 to perform a process of air correction and standardization.

Air correction will now be briefly described. Air correction is made, for example, by dividing a projection image, on an individual energy range basis, by sensitivity/X-ray distribution data, which is measured and prepared before a main imaging operation and stored in the main storage section 109. The sensitivity/X-ray distribution data is prepared for each energy range, for example, by acquiring a projection image on an individual energy basis by irradiating X-rays from the X-ray source 100 without setting a test subject in position, performing averaging in a view direction with respect to the projection image on an individual detection element basis 400, and performing standardization with an average output value in the detection section 104. This correction process is performed for each projection image acquired from respective energy ranges.

Further, still another alternative is to let the signal collection section 108 and the computation section 105 standardize a decrease in the addition rates for a defective element and its diagonal detection element. When, for example, the sum of addition rates for detection elements in a normal pixel is S and the sum of addition rates for a pixel having a defective element is T, the output of the pixel having a defective element is T/S times the output of a pixel having no defective element. Therefore, the output obtained after addition should be increased, for example, by S/T times for standardization purposes.

Consequently, if, for example, detection elements are equal in sensitivity when the correction processing section 1052 provides air correction, and the same dosage is inputted to the detection elements when standardization is not performed, the output value of the pixel 410-2 is ⅚ times the output value of the pixel 410-1. Further, the output value ratio in the sensitivity/X-ray distribution data is also ⅚ times so that the same weight is applied. Therefore, when air correction is made, the addition rates are simultaneously standardized so that the output of the pixel 410-1 is the same as the output of the pixel 410-2.

(An Alternative Time Point for Addition Rate Determination)

The first embodiment has been described above on the assumption that addition rate determination is made by the addition rate determination section 407 after imaging, that is, when a projection image is to be prepared. However, addition rate determination may be made at a different time point, for example, before imaging. Making addition rate determination before imaging eliminates the necessity of determining the addition rates after imaging and reduces the time interval between imaging and projection image completion.

(An Alternative Addition Rate Determination Method Based on the Position of a Defective Element)

Figure 13:
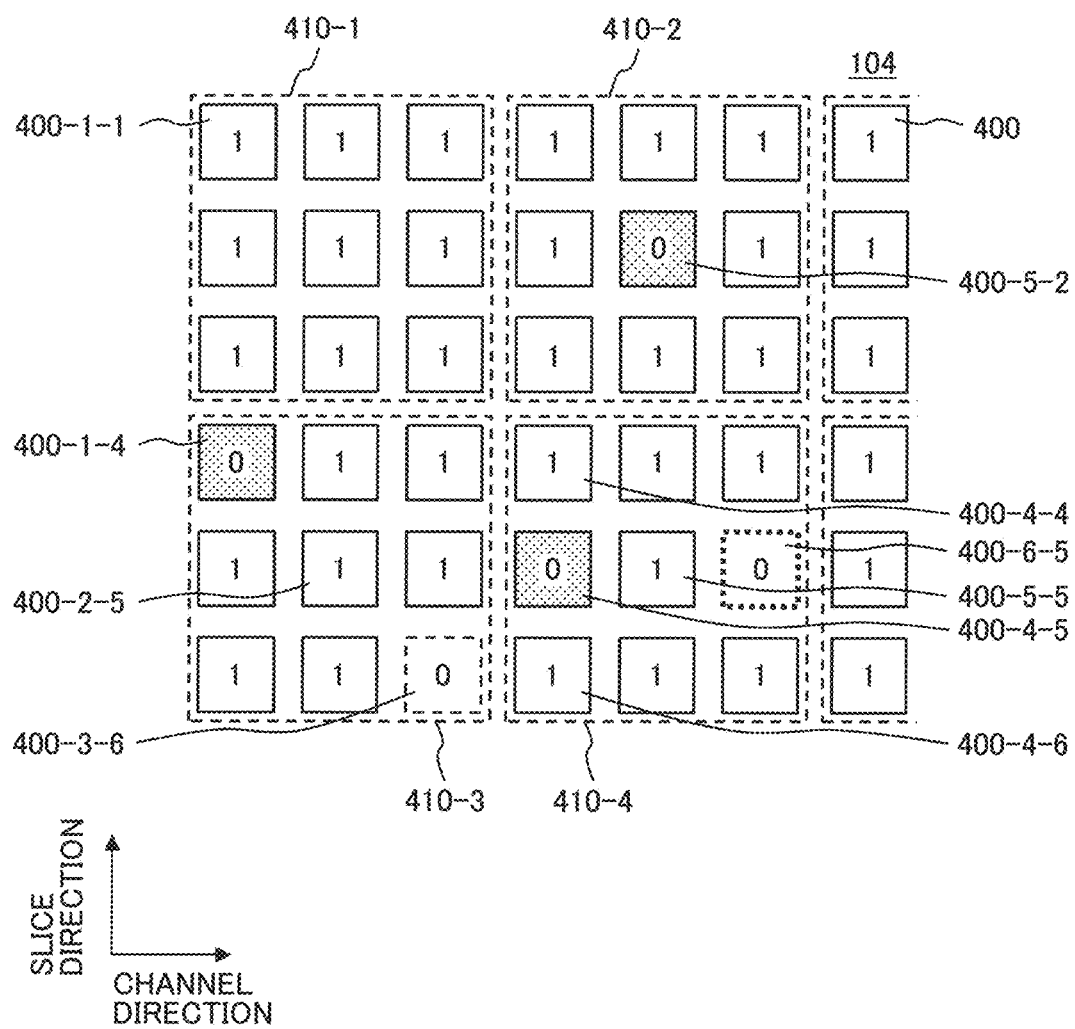
FIG. 13 is a diagram illustrating an exemplary array of the detection elements in the detection section of the X-ray detector according to the first embodiment of the present invention and, in particular, the addition rate for the detection elements.

The above example assumes that when a defective element is positioned neither at a corner of a pixel nor at the center of the pixel, the addition rates for elements around the defective element are increased. However, an alternative is to decrease the addition rate for a diagonal detection element. In this case, for example, the addition rates for the defective element 400-4-5 and its diagonal detection element 400-6-5 may be substantially uniformly decreased. FIG. 13 illustrates an example in which the addition rate decrease amount is 1 and an addition rate of 0 is set. Numerals in the detection elements 400 shown in FIG. 13 denote addition rates. When such addition rates are set, the center of gravity (x, y) of addition rates is identical with the center of a pixel.

The addition rate determination process for the above-mentioned detection elements is performed as outlined below.

First of all, (1) the addition rates for all detection elements are set to 1, and the addition rate for each defective element is decreased by 1. Next, (2) the position of the defective element is checked based on the defective element position information in order to determine whether the defective element is at a corner of a pixel, at the center of the pixel, or at some other position. Subsequently, (3) if the position of the defective element is at a corner of the pixel, the position of a diagonal detection element is determined, and if the diagonal detection element is not defective, its addition rate is decreased by 1. If the position of the defective element is neither at a corner of the pixel nor at the center of the pixel, the position of the diagonal detection element is determined and its addition rate is decreased by 1.

The addition rate determination process performed in the addition rate determination section 407 in the present example will now be described with reference to the flowchart of FIG. 14.

Figure 12:
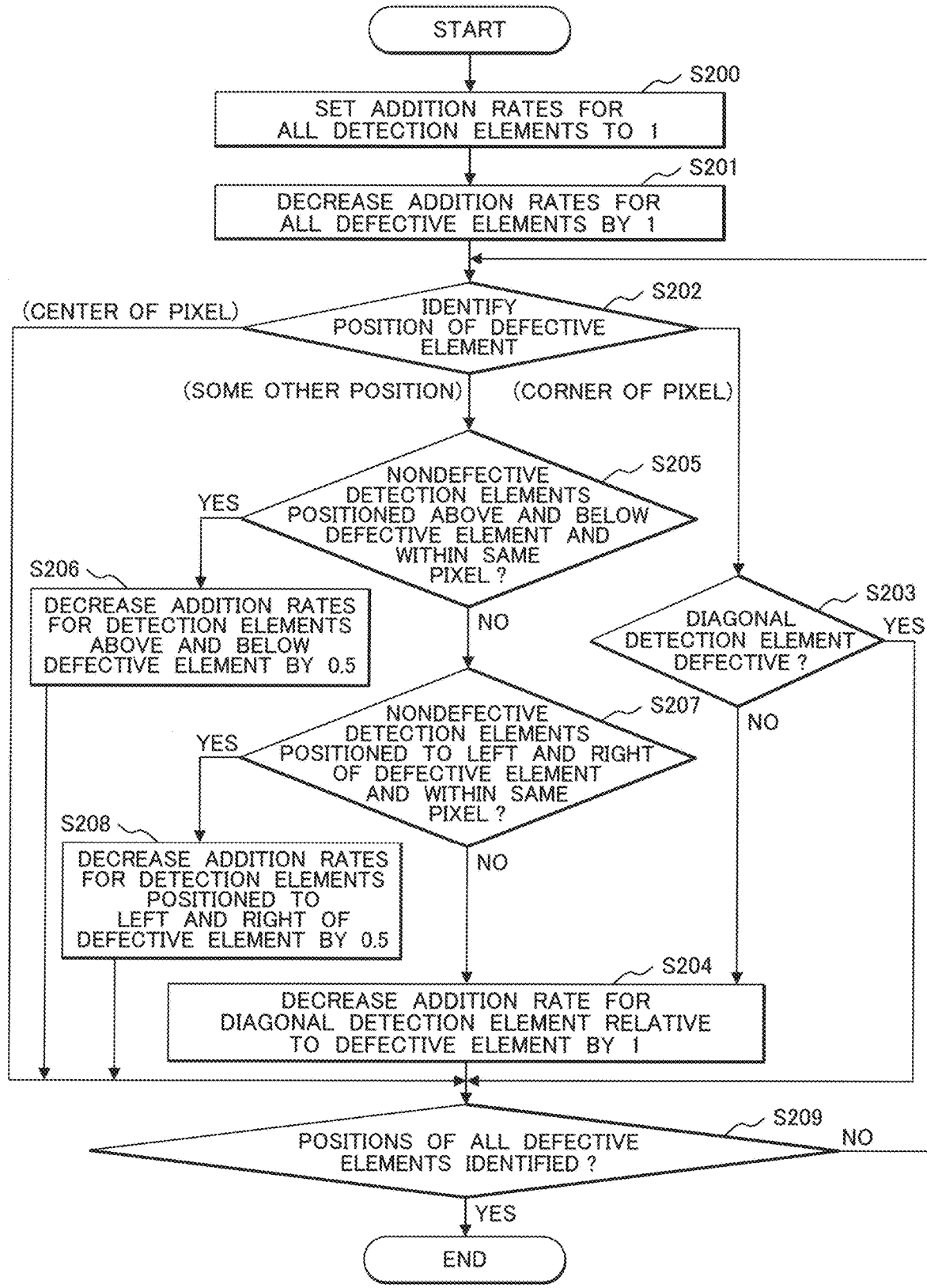
FIG. 12 is a flowchart illustrating an addition rate determination process in an addition rate determination section of the X-ray detector according to the first embodiment of the present invention.
Figure 14:
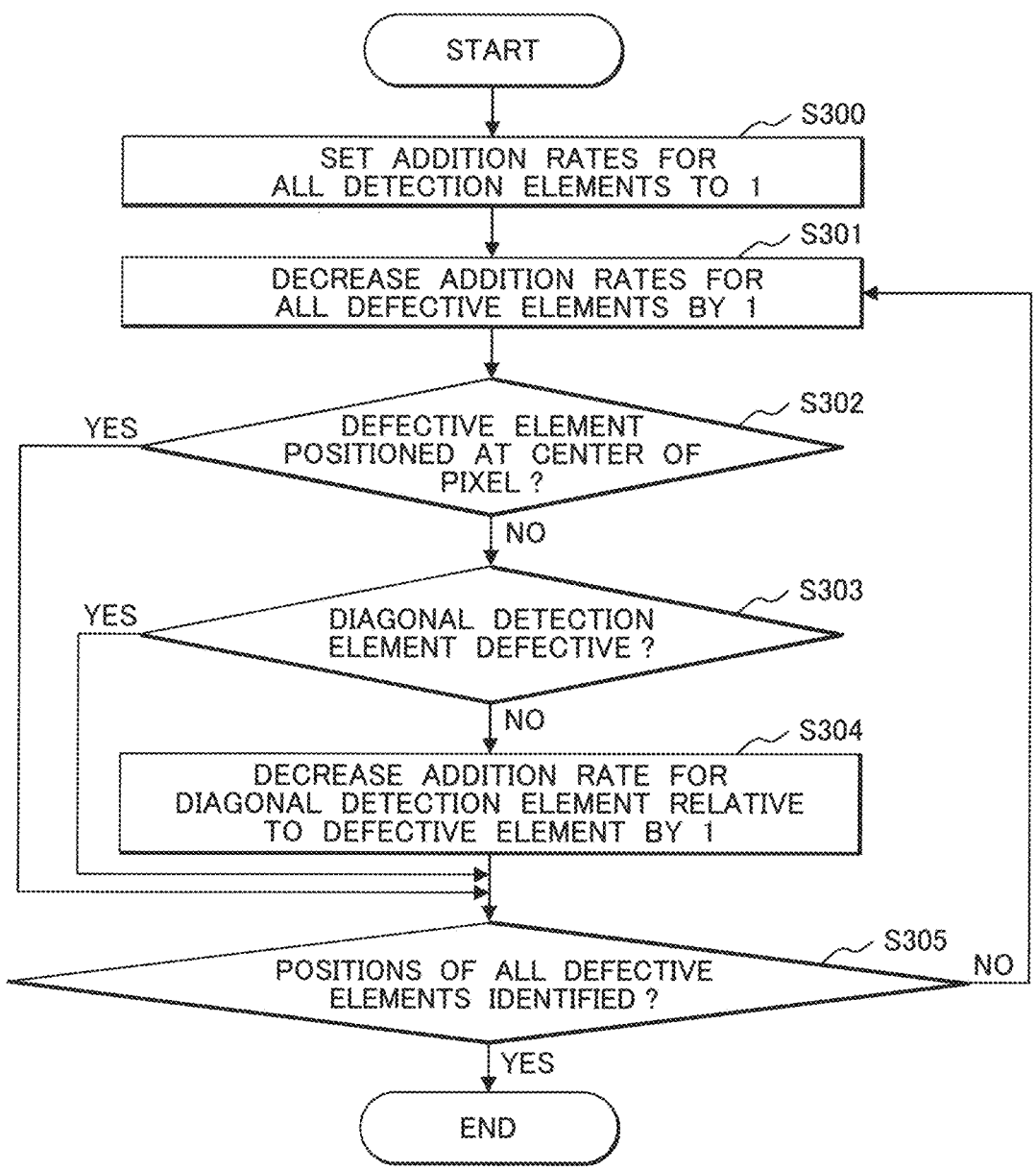
FIG. 14 is a flowchart illustrating another addition rate determination process in the addition rate determination section of the X-ray detector according to the first embodiment of the present invention.

Referring to the flowchart of FIG. 14, in steps S300 and S301, the addition rate determination section 407 sets an addition rate of 1 for all detection elements, as is the case with the flowchart of FIG. 12. Next, the addition rate determination section 407 proceeds to step S201, decreases the addition rates for all defective elements by 1, and then proceeds to step S302. In step S302, the addition rate determination section 407 determines whether a defective element is positioned at the center of a pixel.

If a YES determination result is obtained in step S302, that is, the defective element is positioned at the center of a pixel, processing proceeds to step S305. If, by contrast, a NO determination result is obtained in step S302, that is, the defective element is not positioned at the center of a pixel, processing proceeds to step S303. In step S303, a check is performed to determine whether a diagonal detection element relative to the defective element is defective.

If a NO result is obtained in step S303, that is, the diagonal detection element relative to the defective element is normal, processing proceeds to step S304. In step S304, the addition rate for the diagonal detection element relative to the defective element is decreased by 1. Upon completion of step S304, processing proceeds to step S309.

If, by contrast, a YES result is obtained in step S303, that is, the diagonal detection element relative to the defective element is also defective, processing proceeds to step S305.

In step S305, processing is repeated as needed to determine the positions of all defective elements. After such processing is repeated for all defective elements, the addition rate determination process terminates.

When the above-mentioned defective elements are positioned neither at a corner of a pixel nor at the center of the pixel, the above-described process is slightly inferior in terms of SNR but is simple and suitable for high-speed processing as compared to a case where the addition rates for elements around a defective element are increased.

If, for example, there is one defective element, X-rays are uniformly incident on all detection elements 400, the defective element is positioned neither at a corner of a pixel nor at the center of the pixel, and the addition rates for elements around the defective element are increased, the SNR of the pixel is approximately 7.4% lower than that of a pixel entirely formed of normal detection elements. Meanwhile, if the addition rate for a diagonal detection element is decreased when the defective element is positioned neither at a corner of a pixel nor at the center of the pixel, the SNR of the pixel is 11.8% lower than that of a pixel entirely formed of normal detection elements.

Consequently, it is preferable that a method of decreasing the addition rate for a diagonal detection element to 0 be applied to a case where the center of gravity of addition rates cannot easily be made identical with the center of a pixel by interpolation as in the case where a defective element is at a corner of the pixel.

If, for example, a defective element is positioned at a corner of a pixel, but the output signal of the defective element can be estimated by interpolation in such a manner that the center of gravity is made identical with the center of the pixel by using detection elements of a neighboring pixel, the addition rates for detection elements around the defective element may be increased. That is to say, an appropriate value may be determined by interpolation from neighboring detection elements 400. However, if, for example, it is difficult to place the center of gravity of addition rates at the center of a defective element or it is difficult for the addition section 408 to use the output values of detection elements 400 of a neighboring pixel, it is preferable that the addition rate for a diagonal detection element relative to the defective element be decreased.

The above case corresponds to a situation where, for example, (1) it is difficult for circuits to exchange data before addition because the circuits are formed for each set of blocks of the addition section 408, (2) processing delay occurs, (3) the output values of detection elements belonging to a neighboring detection section 104 cannot easily be exchanged before addition because the relevant pixel is at an end of the detection section 104, (4) it is substantially difficult to perform interpolation with detection elements of a neighboring pixel because the relevant pixel is at an end of an X-ray irradiation field and the neighboring pixel is outside the X-ray irradiation field, (5) the distance to a neighboring pixel is considerable so that low accuracy occurs even when interpolation is performed with the detection elements of the neighboring pixel, or (6) there are substantially no pixels to be sandwiched.

If a defective pixel is at the center of a pixel, an example in which the addition rate for the defective element is decreased by 1 to 0 has been described. However, if addition rate determination is made so that the center of gravity of addition rates is identical with the center of the pixel, the addition rates for detection elements around the defective element can be increased in such a manner as to determine the value of the defective element by performing interpolation from the surrounding detection elements 400.

If the addition rates for the surrounding detection elements 400 are increased, the decrease in the SNR is relatively small when the addition rates for detection elements 400 other than a defective element in a pixel are substantially uniform. However, when the output value of the defective element is determined from the average output value of all detection elements 400 other than the defective element in the pixel, the addition rates for all detection elements 400 in the pixel are identical with each other except for the defective element. Therefore, it can be said that such an addition rate determination method reduces the decrease in SNR by the greatest amount.

(An Alternative Number of Detection Elements in a Pixel)

The foregoing description assumes that the output value of a pixel is determined from 3×3 detection elements. However, the number of detection elements and the method of arraying the detection elements are not limited to the above-described ones. If a pixel is formed of two detection elements and one of the detection elements is defective, the remaining detection element is regarded as a diagonal detection element. When, in this instance, an addition rate of 0 is set for these two detection elements, the output value of the pixel is 0. Consequently, it is preferable that the pixel be formed of three or more detection elements.

Figure 15:
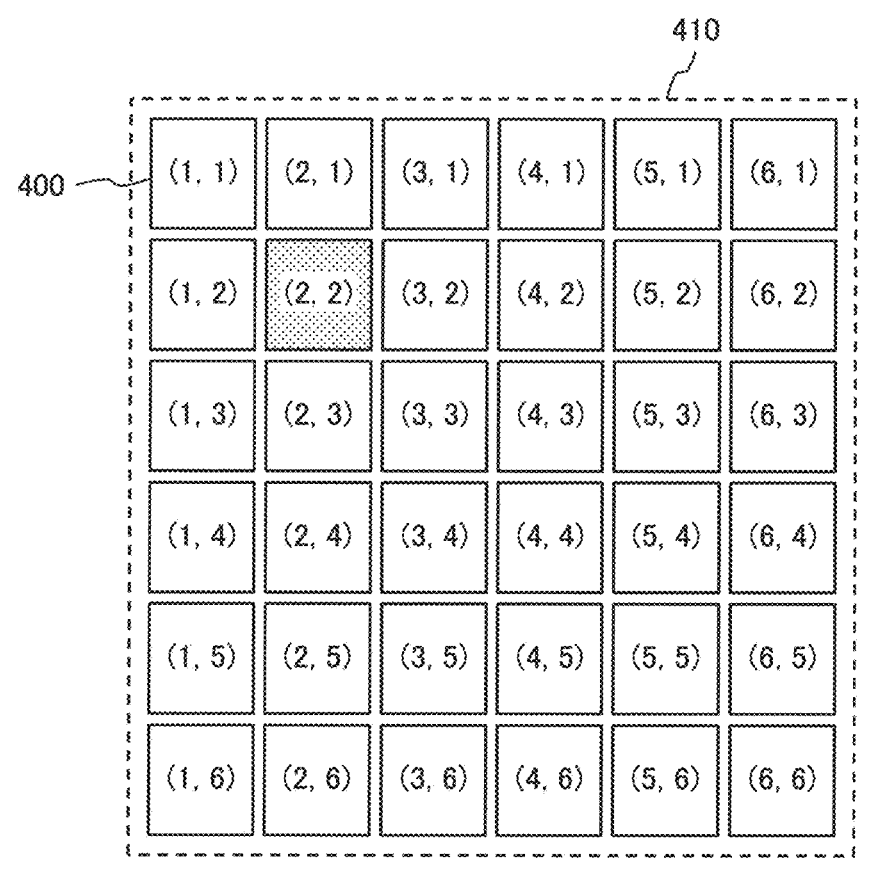

From the viewpoint of SNR, it is preferable that the number of detection elements in a pixel be as large as possible. For example, FIG. 15 illustrates an example in which a pixel 410 is formed of 6×6 detection elements 400. In the example of FIG. 15, a detection element 400 at (2, 2) is defective.

If, in the above case, the addition rate for only the defective element is set to 0, the SNR is 1.4% lower than when there is no defective element. If, by contrast, an addition rate of 0 is set for the defective element and its diagonal detection element (5, 5), the SNR is 2.8% lower than when there is no defective element.

Further, if the pixel is formed of 3×3 detection elements, the decrease in the SNR is 12%.

That is to say, when the pixel includes a large number of detection elements 400, it can be said that the decrease in the SNR is suppressed even if a method of lowering the addition rates for both a defective element and its diagonal detection element is employed.

(An Alternative Mounting Position of the Signal Collection Section 108)

The foregoing description assumes that the signal collection section 108 is disposed on the gantry rotation section 101. However, a part of the signal collection section 108 may alternatively be disposed on a stationary portion. For example, the signal collection section 108 may be a part of the computation section 105.

(A Case where a Pixel has a Plurality of Defective Elements)

The above example assumes that there is only one defective element among a plurality of detection elements forming a pixel. A case where a pixel includes a plurality of defective elements is considered below.

Figure 16:
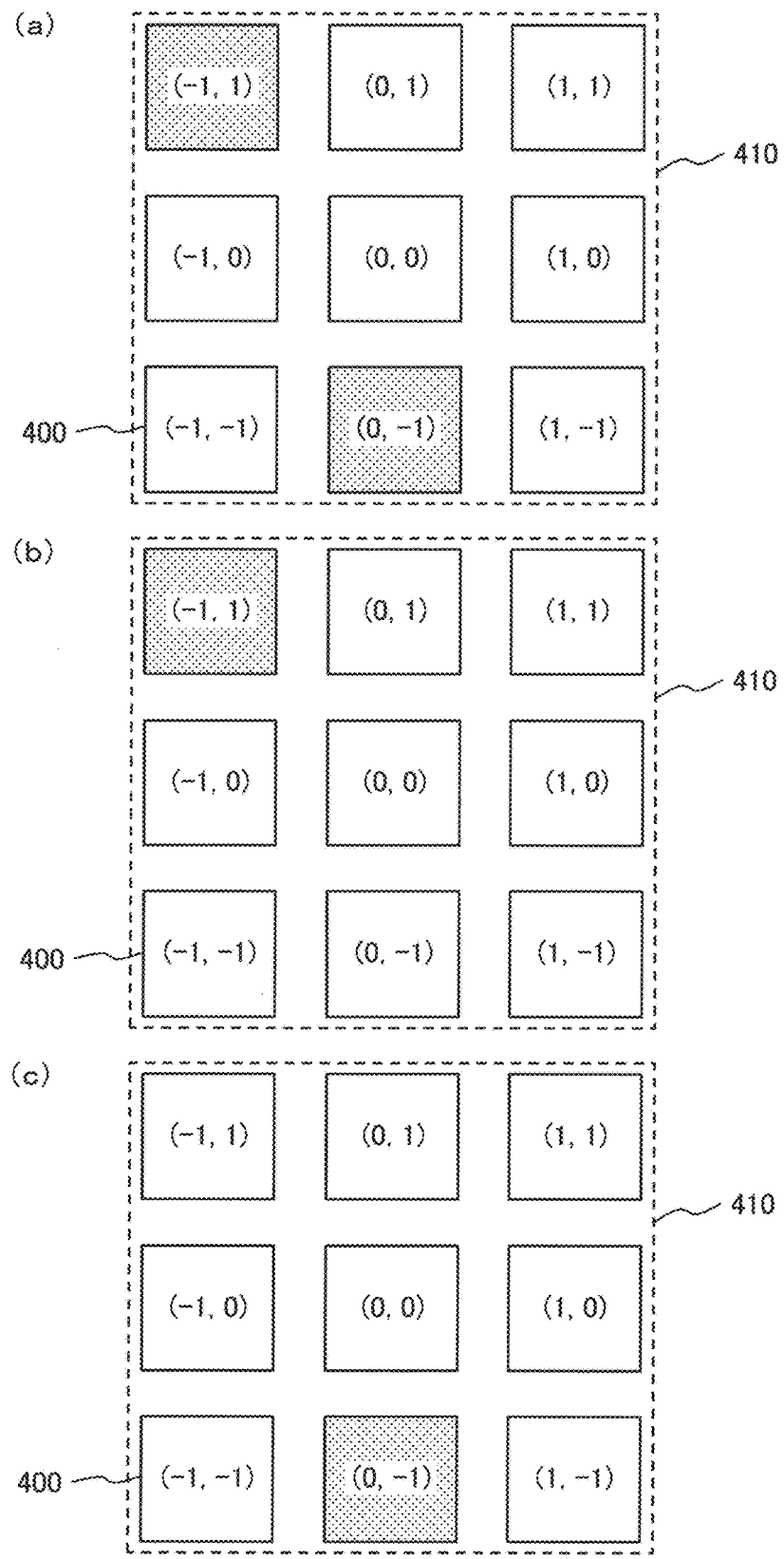
FIG. 16 illustrates an exemplary array of the detection elements in the detection section of the X-ray detector according to the first embodiment of the present invention, (a) illustrates an example in which a pixel includes two defective elements, and diagrams (b) and (c) illustrate an example in which a pixel includes one defective element.

Referring to FIG. 16(*a*), it is assumed that two detection elements 400 at (−1, 1) and (0, 1) are defective. In this instance, FIG. 16(*a*) may be regarded as the combination of FIGS. 16(*b*) and 16(*c*).

Referring to FIG. 16(*b*), the addition rates for a defective element (−1, 1) and a detection element 400 positioned symmetrically with respect to the defective element (−1, 1) about the center of a pixel are decreased by 1.

Referring to FIG. 16(*c*), the addition rates for defective elements 400 positioned at (−1, −1) and (1, −1) and around the defective element are increased by 0.5. In this instance, for the detection element 400 at (1, −1), the addition rate decrease amount is 1, an increase rate is 0.5, and the addition rate is 0.5 (i.e., an addition rate decrease amount of 0.5).

In FIG. 16(*a*), therefore, the addition rate for the detection element 400 at (1, −1) should be set to 0.5, the addition rate for the detection element 400 at (−1, −1) should be set to 1.5, the addition rate for the detection element 400 at (−1, 1) should be set to 0, and the addition rates for the other detection elements 400 should be set to 1. The addition rate in this instance is shown in FIG. 17(*a*).

Further, referring to FIG. 16(*c*), the addition rate for a detection element 400 at (1, 0) serving as a diagonal detection element may be decreased by 1 to 0 as mentioned earlier. The addition rate in this instance is shown in FIG. 17(*b*).

Figure 17:
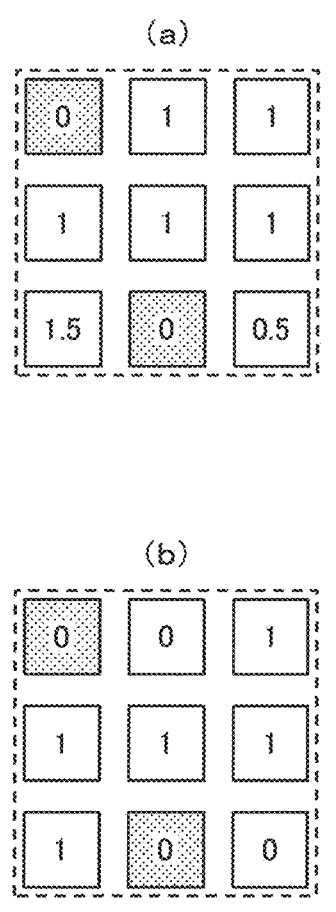

The decrease in the SNR is 14.8% in the example of FIG. 17(*a*) and 25.5% in the example of FIG. 17(*b*). It indicates that the decrease in the SNR is relatively small when the addition rates for detection elements around a defective element are increased.

Further, referring to FIG. 18(*a*) as another example, a case where two detection elements 400 at (−1, 1) and (−1, 0) of one pixel are defective is considered below.

Figure 18:
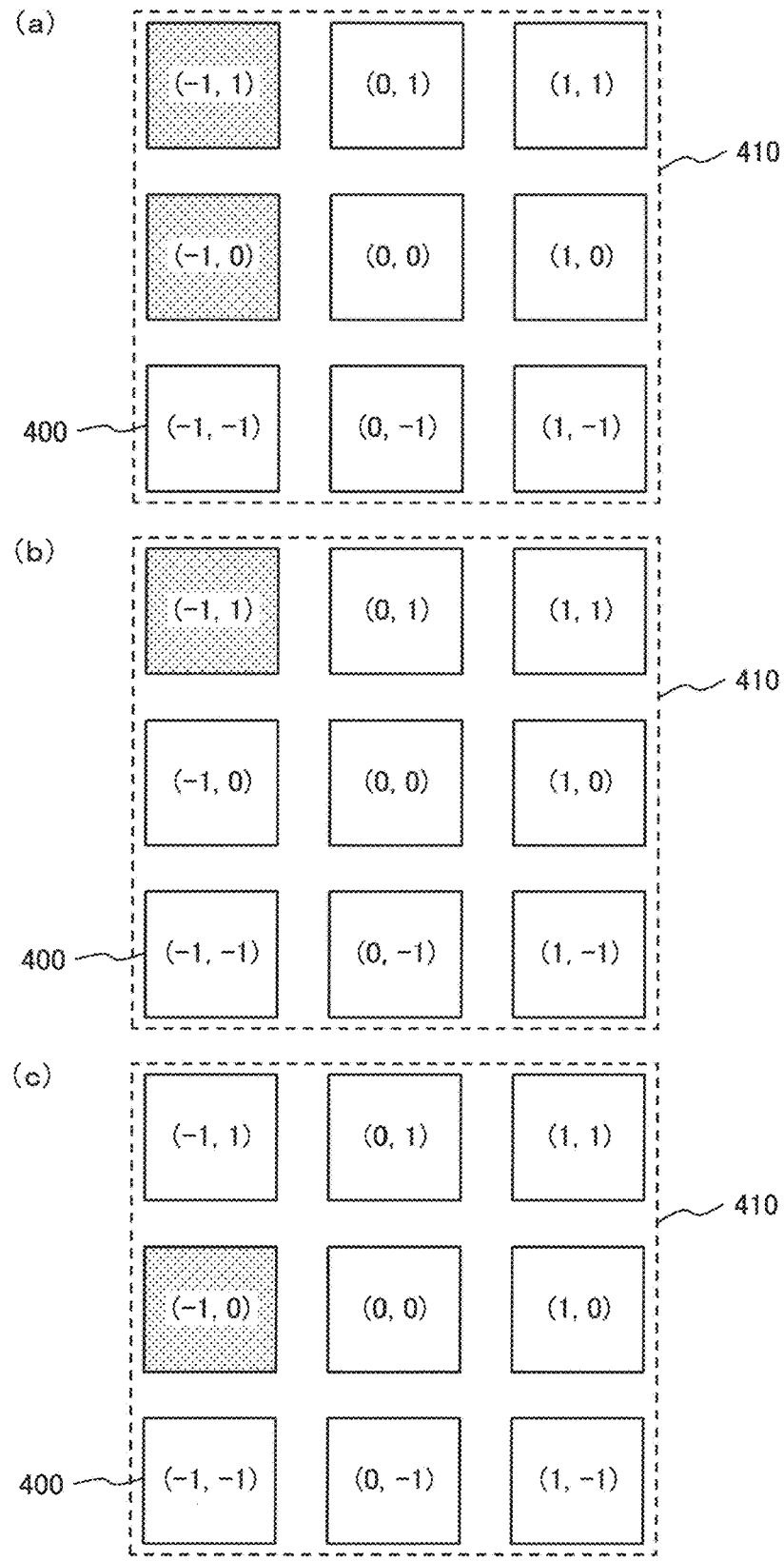
FIG. 18 illustrates an exemplary array of the detection elements in the detection section of the X-ray detector according to the first embodiment of the present invention, (a) illustrates an example in which a pixel includes two defective elements, and (b) and (c) illustrate an example in which a pixel includes one defective element.

Similarly, FIG. 18(*a*) may be regarded as the combination of FIGS. 18(*b*) and 18(*c*).

Referring to FIG. 18(*b*), the addition rate for a diagonal detection element at (1, −1) is decreased by 1.

Meanwhile, referring to FIG. 18(*c*), a detection element 400 at (−1, 1), which is a surrounding detection element, cannot be estimated by interpolation. In FIG. 18(*c*), therefore, the addition rate for a detection element at (1, 0), which is a diagonal detection element, should be decreased by 1.

In view of the above considerations, the addition rates for the defective elements at (−1, 1) and (−1, 0) and the diagonal detection elements at (1, 0) and (1, −1) should be set to 0 (i.e., an addition rate decrease amount of 1), and the addition rates for the other detection elements 400 should be set to 1.

Figure 19:
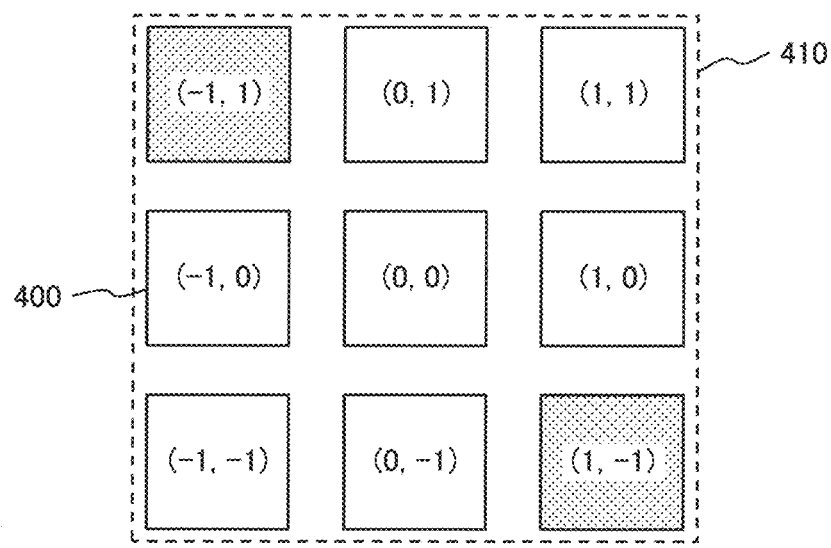
FIG. 19 is a diagram illustrating an exemplary array of the detection elements in the detection section of the X-ray detector according to the first embodiment of the present invention.

Further, FIG. 19 illustrates an example in which detection elements 400 positioned symmetrically about the center of a pixel are defective. Referring to FIG. 19, detection elements at (−1, 1) and (1, 1) are defective. In this case, when an addition rate of 0 is set for the defective elements, the center of gravity of the addition rates is identical with the center of an image. Therefore, the addition rates for the other detection elements need not be decreased.

As described above, even if two defective elements or three or more defective elements are disposed at the other positions, the detection elements 400 for which the addition rates should be decreased can be determined by handling such defective elements as a combination of individual defective elements.

(Alternative Position Information about a Defective Element)

The above examples assume that the array map shown in FIG. 6 is used as the defective element position information. An alternative is, for example, to use an array map formed of numerical values indicating whether the detection elements 400 are normal or defective or use variously shaped array maps.

Further, the defective element position information is not limited to the array map. Information about defective elements only or position information about defective elements only such as coordinates may be stored as the defective element position information. An alternative is to store not only the position information but also the addition rates for the defective elements in association with the position information.

(An Alternative Method of Determining a Diagonal Detection Element)

In the above example, the position of a diagonal detection element for which the addition rate is decreased is determined based on the defective element position information and pixel position information stored in the storage section 406. The pixel position information indicates the positional relationship between a pixel and detection elements 400. The pixel position information indicative of the diagonal detection element for which the addition rate is decreased may be stored in the form of an array map shown, for example, in FIG. 20.

Figure 20:
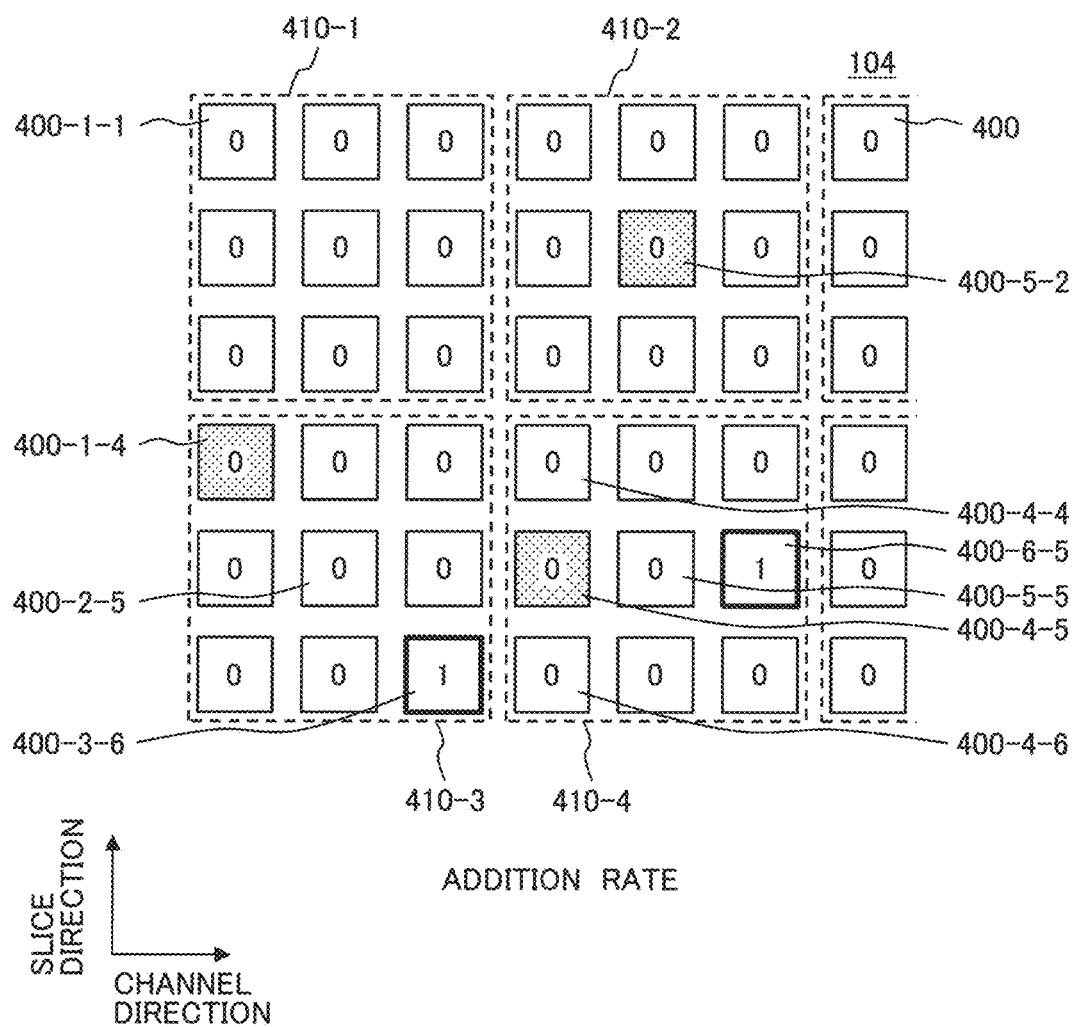
FIG. 20 is a diagram illustrating an exemplary array of the detection elements in the detection section of the X-ray detector according to the first embodiment of the present invention.

FIG. 20 illustrates an example that shows the position of a diagonal detection element in a case where a defective element is at a position indicated in FIG. 6. The diagonal detection element is a detection element 400 that is enclosed by a thick-lined rectangle and marked with "1". As is the case with the position information about a defective element, the position of the diagonal detection element may be stored as variously shaped array maps or as position information such as coordinates.

Figure 21:
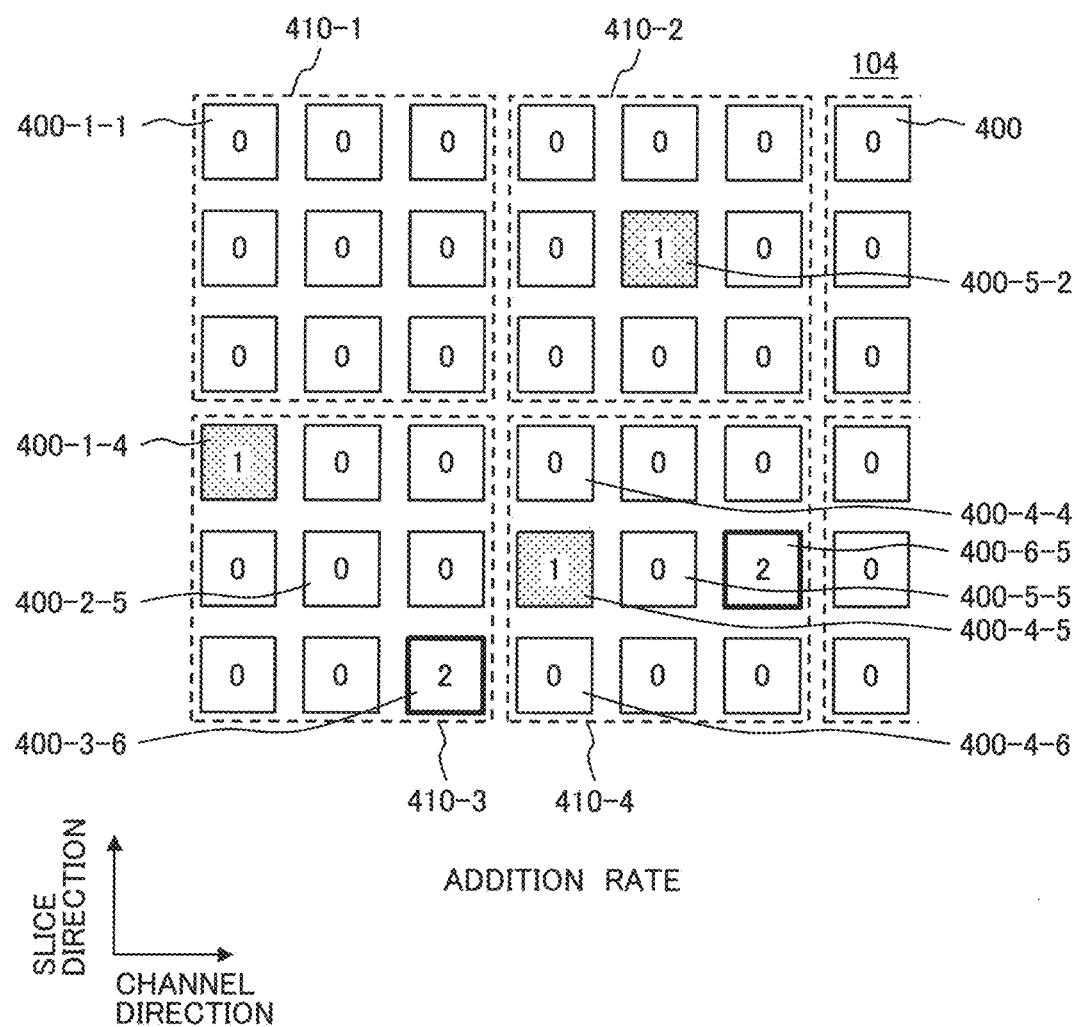
FIG. 21 is a diagram illustrating an exemplary array of the detection elements in the detection section of the X-ray detector according to the first embodiment of the present invention.

Further, the position information about the diagonal detection element for which the addition rate is decreased may be stored together with the defective element position information. That is to say, the pixel position information may double as the defective element position information. FIG. 21 illustrates an example in which the pixel position information doubles as the defective element position information. Referring to FIG. 21, information about the diagonal detection element for which the addition rate is decreased is added to the position information about a defective element and used as the pixel position information. In FIG. 21, normal detection elements 400 for which the addition rate is decreased are marked with "2". In this instance, the addition rate determination section 407 reads the position information about the defective element to simultaneously acquire the position information about the diagonal detection element.

In FIG. 21, detection elements are differentiated from each other by marking normal detection elements with "0", defective elements with "1", and diagonal detection elements with "2". However, such marking is merely an example.

Figure 22:
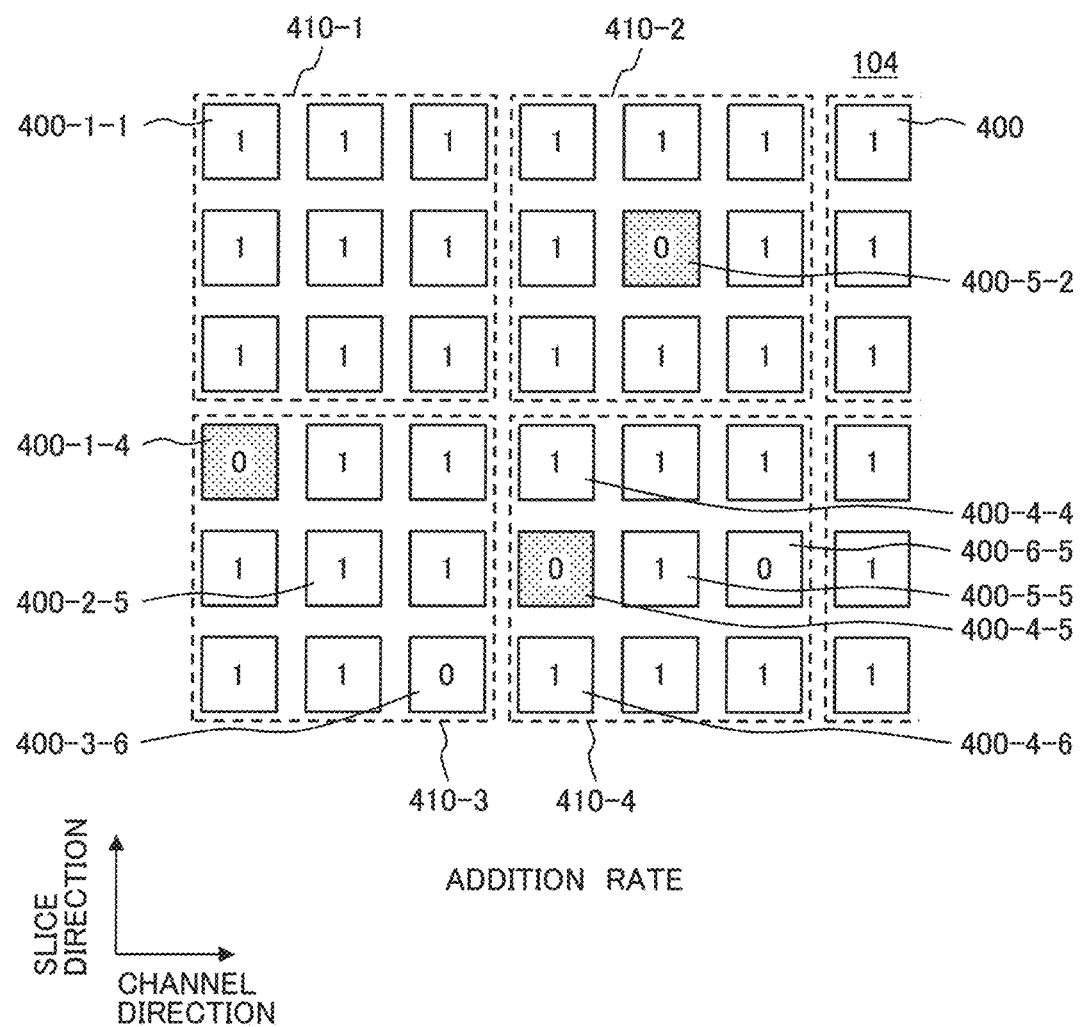
FIG. 22 is a diagram illustrating an exemplary array of the detection elements in the detection section of the X-ray detector according to the first embodiment of the present invention.

Moreover, the position information about a defective element and the pixel position information may include not only the position information about a defective element and a diagonal detection element but also the addition rates. FIG. 22 illustrates an example of pixel position information. Numerals in the detection elements 400 shown in FIG. 22 denote the addition rates. In this instance, when the position information about the defective element is read to acquire the position and addition rate of the diagonal detection element, the addition rate determination section 407 is able to immediately determine the addition rates for all detection elements.

(An Alternative Addition Rate Determination Method)

The foregoing description assumes that the addition rate for a defective element is 0. However, an alternative is to apply various other addition rates that are higher than 0 and lower than 1. When such an alternative is selected in a situation where the detection elements 400 in a pixel are of the same size, the same addition rate decrease amount is set for the defective element and its diagonal detection element so that the center of gravity of the addition rates for the detection elements is identical with the center of the pixel.

Further, the above examples assume that the same addition rate is set for a defective element without regard to the energy range. Alternatively, however, the addition rate decrease amount for the defective element may vary depending on the energy range. A photon-counting detector, in particular, cannot be used in the low energy range because erroneous detection frequently occurs due, for instance, to significant noise generation. In the high energy range, however, the photon-counting detector sometimes performs an accurate counting operation.

In the above case, the addition rates may be set so that only the addition rate for the low energy range is decreased to 0 or higher but lower than 1, and that the addition rate for the high energy range is not decreased. Further, the addition rates may be set so that the addition rate decrease amount for the high energy range is smaller than the addition rate decrease amount for the low energy range.

Moreover, the method of determining the addition rate for a diagonal detection element may vary depending on the energy range. For example, in the pixel 410-4 shown in FIG. 6(a), the addition rates for elements around a defective element may be increased in the low energy range, and the addition rate for a detection element positioned diagonally relative to the defective element may be decreased in the high energy range. As described above, the addition rate for at least either one of a defective element and its diagonal detection element may be varied depending on the energy range.

(An Alternative Array and Shape of Detection Elements)

The present embodiment has been described on the assumption that the detection elements 400 in the detection section 104 are arrayed at equal intervals in both the channel direction and slice direction. However, the addition rates may be determined in the same manner as described in the above examples even if the detection elements are not array at equal intervals. Further, the detection elements 400 need not always have an isotropic shape. Even when the detection elements 400 have an anisotropic shape, the addition rates may be determined in such a manner that the center of gravity of the addition rates is identical with the center of a pixel. In this manner, artifacts are suppressed with ease by enhancing the accuracy of interpolation of defective elements without increasing, for example, the length of processing time, the number of processing circuits, and the amount of interpolation data.

(An Alternative Method of Calculating the Center of Gravity of Addition Rates)

In the above examples, the center of gravity of addition rates is calculated by using the addition rates, that is, by using Equation (3). Alternatively, however, the center of gravity of the addition rates may be calculated from the addition rate decrease amount or increase amount. In such an instance, the center of gravity of the addition rates can be calculated from Equation (6) below by setting the addition rate decrease amount for the detection element 400-$k$ ($k$ is an integer between 1 and N) in Equation (3) to $\beta(k)$ ($=1-\alpha(k)$). If the addition rate decrease amount $\beta(k)$ is negative, it should be regarded as the increase rate.

$$G = -\frac{1}{N}\sum_{k=1}^{N}\beta(k)d(k) \qquad \text{Equation (6)}$$

Equation (6) above is derived from Equation (3) by making use of the fact that the center of gravity of addition rates is identical with the center of a pixel and zero vector when all the addition rates are 1. This method is advantageous in that calculations are easy because only the detection elements for which the addition rates are decreased or increased need to be taken into consideration without considering all the detection elements.

(An Example in which the Detection Elements 400 Differ in Size)

Figure 23:
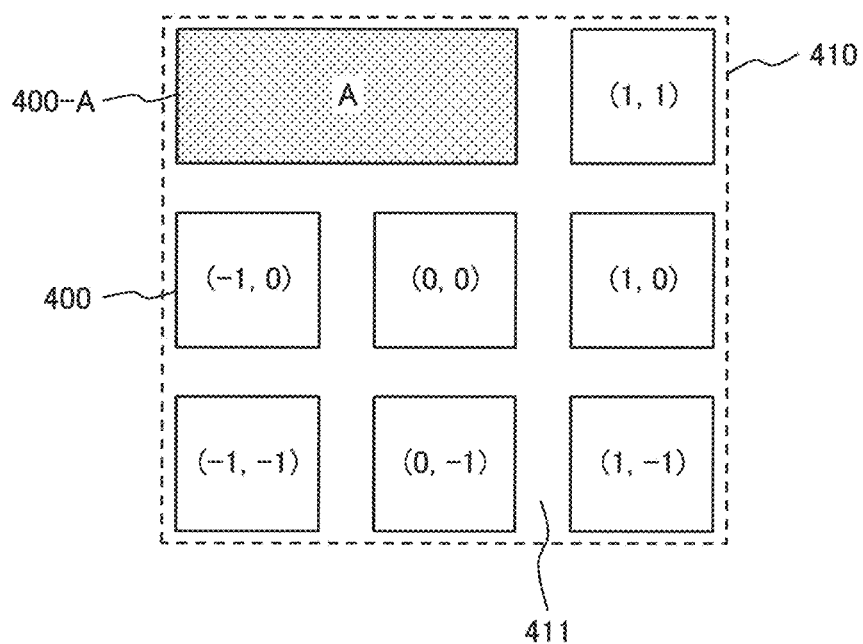
FIG. 23 is a diagram illustrating an exemplary array of the detection elements in the detection section of the X-ray detector according to the first embodiment of the present invention.

The present embodiment has been described on the assumption that the detection elements included in a pixel are of the same size. However, the detection elements included in one pixel need not always be equal in size. The detection elements included in one pixel may differ in size as illustrated, for example, in FIG. 23.

In the above case, the center of gravity of addition rates is to be determined in a different manner. If the detection elements included in one pixel are equal in size, that is, in area, the sum of products of a vector from a start point to the center of a detection element 400 and its addition rate can be standardized by the number of detection elements 400 in accordance with Equation (3).

However, if the detection elements are not equal in area, the addition rate for each detection element needs to be weighted based on its area. That is to say, area weighting needs to be performed on the product of the vector from the start point to the center of a detection element and its addition rate. Therefore, when the area of a detection element $k$ ($k$ is an integer between 1 and N) is S($k$) and the total area of detection elements in a pixel is $S_{all}$, the center of gravity G of the addition rates can be expressed by Equation (7) below.

$$G = \frac{1}{NS_{all}} \sum_{k=1}^{N} S(k)\alpha(k)d(k) \qquad \text{Equation (7)}$$

Here, the area ratio of a detection element may be used instead of the area S(k). In this instance, the sum of area ratios may be used as the total area $S_{all}$. Accordingly, when, in the example of FIG. 23, an addition rate of 0 is to be set for a detection element 400-A, which is a defective element, the addition rates for detection elements at (0, −1) and (1, −1) should also be set to 0. In this instance, the total area of the detection elements at (0, −1) and (1, −1) looks smaller than the area of the detection element 400-A by a space 411 between the detection elements at (0, −1) and (1, −1).

When, for example, the detection elements are formed of a semiconductor material, an electrical charge generated by X-rays falling into the space 411 is detected by either the detection element at (0, −1) or the detection element at (1, −1). Therefore, the space 411 can be substantially regarded as 0. Consequently, the sum of the areas of the detection elements at (0, −1) and (1, −1) may be regarded as being equal to the area of the detection element 400-A.

That is to say, when the detection elements in a pixel are of the same size, the addition rate decrease amount for a diagonal detection element needs to be the same as for a defective element. Meanwhile, if the detection elements in a pixel are different in size, the addition rate decrease amount for the diagonal detection element needs to be determined in such a manner that the product of the addition rate decrease amount for the diagonal detection element and its area is equal to the product of the addition rate decrease amount for the defective element and its area.

To put it another way, when the addition rate decrease amount for a diagonal detection element having the same area as a defective element is to be equal to the addition rate decrease amount for the defective element, it is necessary to select a diagonal detection element having the same area as the defective element. That is to say, the addition rate decrease amount for the diagonal detection element needs to be determined by multiplying the addition rate decrease amount for the defective element by the area ratio between the defective area and the diagonal detection element. In this instance, it is preferable that the total diagonal detection element area be equal to or larger than the area of the defective element in order to prevent the addition rate decrease amount from being 1 or larger. To put it still another way, the rear of the diagonal detection element needs to be determined by multiplying the area of the defective element by the addition rate decrease amount ratio between the defective element and the diagonal detection element.

If detection elements positioned symmetrically about the center of a pixel are of the same in a situation where detection elements included in a pixel differ in size, it is possible to use the method of decreasing the addition rates for the symmetrically positioned detection elements.

When the addition rates are to be determined in consideration of area information such as the information about area and area ratio, the addition rates can be determined, for example, by performing the procedure described below.

(1) Set an addition rate of 1 for all detection elements and decrease the addition rate for a defective element by 1.

(2) Identify the position of the defective element by determining whether it is at a corner, the center, or some other position of a pixel.

(3) If the defective element is positioned at a corner of the pixel, determine the position of a diagonal detection element, divide the area of the defective element by the area of the diagonal detection element, multiply the result of the division by the addition rate decrease amount for the defective element (=the area of the defective element=the area of the diagonal detection element×the addition rate decrease amount for the defective element), and decrease the addition rate for the diagonal detection element by the result of the multiplication. If the defective element is positioned neither at a corner of the pixel nor at the center of the pixel, increase the addition rates for elements surrounding the defective element in such a manner that the output of the defective element is interpolated by the surrounding elements.

(4) Standardize the difference in the sum of the addition rates between the pixels.

If there are a plurality of defective elements, the addition rates can be determined by repeating steps (2) and (3) of the above procedure for each defective element. In step (1) above, it is assumed that the addition rates for all detection elements are 1. However, an alternative is to use a uniform addition rate of greater than 0.

If the addition rate for the diagonal detection element is to be decreased in a situation where the defective element is positioned neither at a corner of a pixel nor at the center of the pixel, it is preferable that step (3') below be performed instead of step (3).

(3') If the defective element is at a position other than the corner of the pixel and other than the center of the pixel, determine the position of the diagonal detection element, divide the area of the defective element by the area of the diagonal detection element, multiply the result of the division by the addition rate decrease amount for the defective element, and decrease the addition rate for the diagonal detection element by the result of the multiplication.

(An Alternative Detection Section)

The present embodiment has been described on the assumption that the detection section 104 applies a semiconductor detector for directly detecting X-rays. However, an alternative is to use a detector formed of a scintillator and a semiconductor photodetector. When such an alternative configuration is employed, X-rays are detected and converted to light, and then the light is converted to an electrical signal by the semiconductor photodetector. These conversion sequences are performed for each X-ray photon, and the resulting electrical signal is used to perform energy separation of incident X-rays.

Second Embodiment

A second embodiment of the present invention will now be described. The second embodiment differs from the first embodiment in that the X-ray detector includes the detection section 104 and signal collection section 108 for adding an analog signal and then converting the resulting signal to a digital signal. As an example of such a configuration, a case where a so-called integrated X-ray detector is used is described below.

Figure 24:
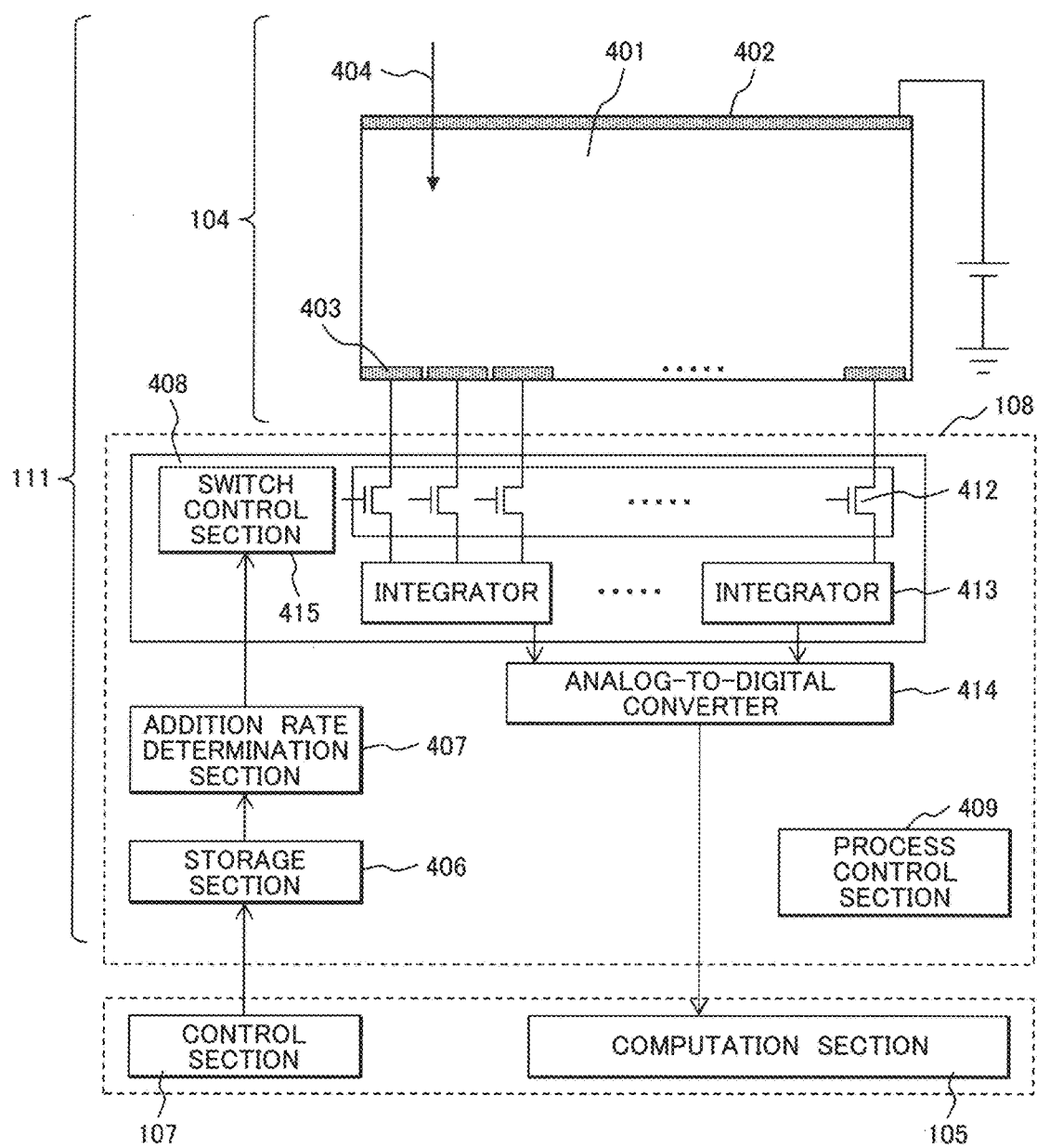
FIG. 24 is a block diagram illustrating an overview of the X-ray detector according to a second embodiment of the present invention.

As illustrated in FIG. 24, the X-ray detector 111 includes the detection section 104 and the signal collection section 108. The signal collection section 108 includes the process control section 409, the addition rate determination section 407, the storage section 406, the addition section 408, and an analog-to-digital converter 414. The detection section 104 will not be described in detail because it has the same configuration as the counterpart of the first embodiment. Further, the addition rate determination section 407 and the storage section 406 are identical with the counterparts of the first embodiment and will not be described in detail.

The addition section 408 includes a plurality of switches 412, a plurality of integrators 143, a switch control section 415, and the analog-to-digital converter 414.

While the above-described configuration is employed, the switch control section 415 determines the on/off states of the switches 412 for each detection element 400 in order to provide the addition rates determined by the addition rate determination section 407, and the integrator 413 integrates only the electrical charge of a turned-on detection element 400. This integration adds the electrical charge of a detection element 400 for which a switch 412 is turned on, and allows the analog-to-digital converter 414 to convert the output voltage of the integrator 413 to a digital signal and output the digital signal to the computation section 105.

As described above, the switch control section 415 in the present embodiment provides an addition rate of 0 by turning off the switches 412 and provides an addition rate of 1 by turning on the switches 412. Further, as is the case with the first embodiment, the addition rate determination section 407 uses, for example, the defective element position information stored in the storage section 406 to decide on setting an addition rate of 0 (i.e., an addition rate decrease amount of 1) for a defective detection element and its diagonal detection element and an addition rate of 1 for the other detection elements.

Figure 25:
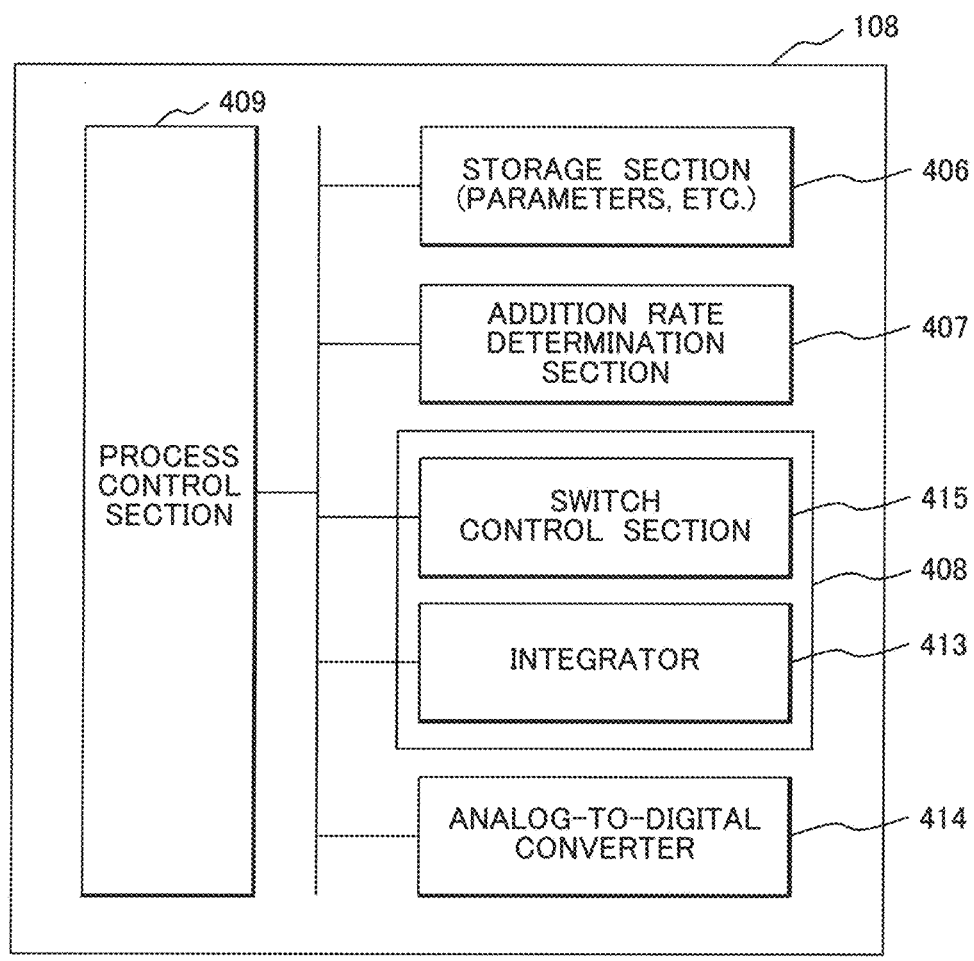
FIG. 25 is a block diagram illustrating an overview of a signal processing section in the X-ray detector according to the second embodiment of the present invention.

As illustrated in FIG. 25, elements of the signal collection section 108 are controlled by the process control section 409. First of all, the defective element position information stored in the storage section 406 is used to exercise control before an imaging operation so that the addition rate determination section 407 determines the addition rates. Next, the switch control section 415 is controlled to provide the addition rates, which are to be persistently retained during a subsequent imaging operation. Further, during an actual imaging operation, control is exercised so that an analog signal is integrated by the integrator 413 and converted to a digital signal by the analog-to-digital converter 414.

In the X-ray CT device incorporating the X-ray detector 111 for adding an analog signal and then converting the analog signal to a digital signal, an element made defective due, for instance, to a defect shifts the sampling position of a projection image pixel and thus alters the output value. This further results in the generation of artifacts. However, the above-described configuration makes it possible to easily avoid or reduce the generation of artifacts and obtain an accurate output value.

(An Alternative Number of Detection Elements on which an Addition Process is Performed)

In the present embodiment, one integrator is provided for each set of three detection elements. However, the number of detection elements in each set is not limited to three. Alternatively, one integrator may be provided for each set of four or more detection elements. Further, the addition of output signals from two-dimensionally arrayed detection elements may be performed as well as the addition of output signals from only one-dimensionally arrayed detection elements.

(An Alternative X-Ray Detector)

In the present embodiment, the X-ray detector 111 is of an integrated type. However, the use of an integrated X-ray detector is merely an example. The present invention is not limited to the use of an integrated X-ray detector. For example, a photon-counting X-ray detector may be used. In this instance, integration of an electrical charge generated by X-rays and conversion to a digital signal are performed for each X-ray photon. Another alternative is to use an energy-separation X-ray detector. In this instance, energy separation and analog-to-digital conversion may be performed by the analog-to-digital converter 414.

(An Example in which the Detection Elements Differ in Size)

The present embodiment has been described on the assumption that the detection elements included in a pixel are of the same size. However, the detection elements included in one pixel need not always be equal in size. As is the case with the first embodiment, when a defective element and its diagonal detection element differ in size, the addition rate decrease amount for the diagonal detection element should be determined so that the product of the addition rate decrease amount for the diagonal detection element and its area is equal to the product of the addition rate decrease amount for the defective element and its area.

In the present embodiment, the switches 412 are turned on or off to provide the addition rates. Therefore, only an addition rate of 0 or 1 can be provided. Consequently, it is preferable that the above-described method be applied when the area ratio between a defective element and its diagonal detection element is an integer ratio. However, even if the area ratio is not an integer ratio, the center of gravity of the addition rates approaches the center of a pixel to reduce the alteration of the output value of the pixel as far as the addition rate decrease amount for the diagonal detection element is determined in such a manner that the product of the addition rate decrease amount for the diagonal detection element and its area is close to the product of the addition rate decrease amount for the defective element and its area.

(An Alternative Device Configuration)

The first and second embodiments have been described on the assumption that an X-ray detector is applied to an X-ray CT device. However, an alternative is to use the X-ray detector 111 independently or apply the X-ray detector 111 to a different X-ray imaging device and various other devices.

The present invention is not limited to the above-described embodiments. It is to be understood that various modifications may be made without departing from the spirit and scope of the present invention. The above-described embodiments include various stages so that a variety of inventions may be developed by combining a plurality of disclosed elements. For example, some of the elements described in conjunction with the above-described embodiments may be removed. An example of this would be a device not adapted to perform an image reconstruction process or a device having no X-ray source, namely, for example, an X-ray diagnostic imaging device, an X-ray imaging device, an X-ray fluoroscopy device, a mammography device, a digital subtraction device, an X-ray detector, or a radiation detector.

Further, the present invention is not only applicable to an X-ray detector and a radiation detector, but also applicable, for example, to a detector adapted to detect photons having various wavelengths, such as a visible light detector or an infrared detector, and to a detection device or imaging device having such a detector.

The present invention relates to an X-ray detector for determining the output value of a pixel for a projection image by adding the outputs of a plurality of detection elements, and makes it easy to reduce or avoid the alteration of the output value, which is caused by a pixel sampling position shift due to defective elements, without increasing, for example, the length of processing time, the number of processing circuits, and the amount of interpolation data. As a result, the accuracy of interpolation of the defective elements can be enhanced to suppress artifacts with ease.

REFERENCE SIGNS LIST

104 . . . detection section,
105 . . . computation section,
106 . . . display section
107 . . . control section
108 . . . signal collection section
110 . . . input section
111 . . . X-ray detector
405 . . . readout circuit
406 . . . storage section
407 . . . addition rate determination section
408 . . . addition section

The invention claimed is:

1. An X-ray detector comprising:
a detection section that includes a plurality of detection element groups obtained by forming a two-dimensional array of detection elements for detecting X-rays, and forms a plurality of arrays of the detection element groups corresponding to one pixel;
an addition rate determination section that determines addition rates for output signals of the detection elements;
an addition section that calculates the signal value of each pixel of a projection image by adding the output signals of the detection elements belonging to the detection element groups in accordance with the addition rates; and
a position information storage section that stores pixel position information and defective element position information, the pixel position information indicating the positional relationship between the pixel and the detection elements belonging to a detection element group corresponding to the pixel, the defective element position information indicating the position of a defective element included in the detection element group;
wherein, based on the pixel position information and the defective element position information, the addition rate determination section determines the addition rate for the output signal of the defective element included in a pixel targeted for signal value calculation and the addition rate for the output signal of a diagonal detection element positioned symmetrically with respect to the defective element about the center of the pixel targeted for signal value calculation in such a manner that the addition rates are equal and lower than the addition rates for the other detection elements and that the addition rates for the other detection elements are substantially equal.

2. The X-ray detector according to claim 1, wherein the position information storage section stores area information including information about the areas or area ratios of the detection elements; and wherein the addition rate determination section determines, based on the area information, the addition rates for the defective element and the diagonal detection element.

3. The X-ray detector according to claim 1, wherein the addition section includes a digital conversion section that converts the output signals of the detection elements to digital signals, and calculates the signal value of each pixel of the projection image by adding the digital signals of the detection elements belonging to the detection element group in accordance with the addition rates.

4. The X-ray detector according to claim 1,
wherein the addition section includes an analog signal addition section that calculates an analog output value by adding analog output signals from the detection elements on an individual pixel basis in accordance with the addition rates, and a digital conversion section that converts the analog output value of the pixel to a digital signal; and
wherein the addition rate determination section determines the addition rates by turning switches on or off.

5. The X-ray detector according to claim 1, wherein the addition rates for the defective element and the diagonal detection element are 0.

6. The X-ray detector according to claim 1,
wherein the addition rate determination section identifies the arrayed position of the defective element in the detection element group; and
wherein, when the defective element is at a position other than the center of the detection element group, the addition rates for both the defective element and the diagonal detection element are determined to be 0.

7. The X-ray detector according to claim 6,
wherein the addition rate determination section identifies the arrayed position of the defective element in the detection element group; and
wherein, when the defective element is positioned at a corner in the detection element group, the addition rates for the defective element and the diagonal detection element are determined to be 0.

8. The X-ray detector according to claim 1,
wherein the position information storage section stores beforehand the addition rates for the detection elements as addition rate information; and
wherein the addition rate determination section uses the addition rate information to determine the addition rates for the detection elements.

9. The X-ray detector according to claim 1, further comprising:
a standardization section that standardizes the signal value of each pixel of the projection image in accordance with the sum of addition rates for the detection elements belonging to the detection element group.

10. The X-ray detector according to claim 3,
wherein the detection elements detect X-rays and generate a signal from the detected X-rays, the generated signal being based on the energy of X-ray photons;
wherein the digital conversion section separates the energy into two or more energy ranges and outputs a digital signal based on the number of X-ray photons; and
wherein the addition section calculates the signal value of the pixel for each of the energy ranges.

11. The X-ray detector according to claim 10, wherein at least either one of the addition rates for the defective element and the diagonal detection element varies from one energy range to another.

12. An X-ray CT device comprising:
the X-ray detector according to claim 1;
an X-ray generation section that irradiates X-rays;
a reconstruction processing section that prepares a reconstructed image by performing a reconstruction computation on a signal from the X-ray detector; and
a control section that controls the X-ray detector, the X-ray generation section, and the reconstruction processing section.

13. An X-ray detection method that relates to an output signal generated by a detection section in accordance with the amount of electrical charge, the detection section being configured to include a plurality of detection element groups obtained by forming a two-dimensional array of detection elements for detecting X-rays and form a plurality of arrays of the detection element groups corresponding to one pixel of a projection image, the X-ray detection method comprising the steps of:

storing pixel position information and defective element position information, the pixel position information indicating the positional relationship between the pixel and the detection elements belonging to a detection element group corresponding to the pixel, the defective element position information indicating the position of a defective element included in the detection element group;

based on the pixel position information and the defective element position information, determining the addition rate for the output signal of the defective element included in a pixel targeted for signal value calculation and the addition rate for the output signal of a diagonal detection element positioned symmetrically with respect to the defective element about the center of the pixel targeted for signal value calculation in such a manner that the addition rates are equal and lower than the addition rates for the other detection elements and that the addition rates for the other detection elements are substantially equal; and calculating the signal value of each pixel of the projection image by adding the output signals of the detection elements belonging to the detection element group in accordance with the addition rates.

14. A processor or a non-transitory medium with [a]n X-ray detection program that relates to an output signal generated by a detection section in accordance with the amount of electrical charge, the detection section being configured to include a plurality of detection element groups obtained by forming a two-dimensional array of detection elements for detecting X-rays and form a plurality of arrays of the detection element groups corresponding to one pixel of a projection image, the X-ray detection program stored on the processor or the non-transitory medium and configured to perform the steps of:

storing pixel position information and defective element position information, the pixel position information indicating the positional relationship between the pixel and the detection elements belonging to a detection element group corresponding to the pixel, the defective element position information indicating the position of a defective element included in the detection element group;

based on the pixel position information and the defective element position information, determining the addition rate for the output signal of the defective element included in a pixel targeted for signal value calculation and the addition rate for the output signal of a diagonal detection element positioned symmetrically with respect to the defective element about the center of the pixel targeted for signal value calculation in such a manner that the addition rates are equal and lower than the addition rates for the other detection elements and that the addition rates for the other detection elements are substantially equal; and calculating the signal value of each pixel of the projection image by adding the output signals of the detection elements belonging to the detection element group in accordance with the addition rates.

\* \* \* \* \*